(12) United States Patent
Ferapontova

(10) Patent No.: US 11,807,893 B2
(45) Date of Patent: Nov. 7, 2023

(54) METHOD AND ELECTRONIC DEVICE FOR DETERMINING THE CONCENTRATION OF AN ANALYTE

(71) Applicant: Numen Sensorics ApS, Egå (DK)

(72) Inventor: Elena Ferapontova, Egå (DK)

(73) Assignee: Numen Sensorics ApS, Egå (DK)

( * ) Notice: Subject to any disclaimer, the term of this patent is extended or adjusted under 35 U.S.C. 154(b) by 552 days.

(21) Appl. No.: 16/025,608

(22) Filed: Jul. 2, 2018

(65) Prior Publication Data

US 2019/0002948 A1 Jan. 3, 2019

(30) Foreign Application Priority Data

Jul. 3, 2017 (EP) .................................... 17179278

(51) Int. Cl.
*C12Q 1/00* (2006.01)
*C12Q 1/6825* (2018.01)
(Continued)

(52) U.S. Cl.
CPC ........... *C12Q 1/005* (2013.01); *C12Q 1/6825* (2013.01); *G01N 27/3276* (2013.01);
(Continued)

(58) Field of Classification Search
None
See application file for complete search history.

(56) References Cited

U.S. PATENT DOCUMENTS 5,547,848 A * 8/1996 Shinoki ................ G01N 33/558
436/514
5,972,692 A * 10/1999 Hashimoto ........ G01N 27/3276
435/287.2
(Continued)

FOREIGN PATENT DOCUMENTS

WO WO2009/039136 A2 3/2009
WO WO2011/150186 A1 12/2011

OTHER PUBLICATIONS

Nakazawa et al. Hybrid Nanocellulosome Design from Cellulase Modules on Nanoparticles: Synergistic Effect of Catalytically Divergent Cellulase Modules on Cellulose Degradation Activity. ACS Catal.; 2013; 3: 1342-1348. (Year: 2013).*
(Continued)

*Primary Examiner* — Robert T. Crow
(74) *Attorney, Agent, or Firm* — Julie K. Staple; Dinsmore & Shohl LLP

(57) ABSTRACT

A method is provided for determining, the presence and concentration of an analyte by contacting the sample with a solution comprising: magnetic beads, a capture probe capable of binding the analyte, a reporter probe and cellulose, whereby, if the analyte is present, an MB-analyte-reporter-cellulase sandwich is formed; and then contacting the solution comprising the sandwich with an electrode covered with an electrically insulating layer comprising or consisting of cellulose and/or a cellulose derivative, wherein the MB-analyte-reporter-cellulase sandwich leads to degradation of the insulating layer thereby causing a measurable change in electrical properties at the electrode surface, wherein the change in electrical properties is a function of the amount of analyte in the sample. Devices and biosensor applying the method are also provided.

7 Claims, 14 Drawing Sheets

Specification includes a Sequence Listing.

(51) Int. Cl.
*G01N 27/327* (2006.01)
*G01N 27/22* (2006.01)

(52) U.S. Cl.
CPC ....... *G01N 27/3277* (2013.01); *G01N 27/227* (2013.01); *G01N 2333/942* (2013.01); *G01N 2446/00* (2013.01)

(56) References Cited

U.S. PATENT DOCUMENTS

| | | | | |
|---|---|---|---|---|
| 2009/0042200 | A1* | 2/2009 | Okano | A01N 1/0284 435/6.12 |
| 2011/0171749 | A1* | 7/2011 | Alocilja | B82Y 5/00 536/23.1 |
| 2014/0323948 | A1* | 10/2014 | Ek | A61N 1/0531 604/20 |
| 2014/0327504 | A1* | 11/2014 | Hakman | C08L 1/02 336/55 |
| 2015/0027891 | A1* | 1/2015 | Puleo | C12N 15/101 204/543 |

OTHER PUBLICATIONS

Fapyane and Ferapontova. Electrochemical Assay for a Total Cellulase Activity with Improved Sensitivity. Anal. Chem; Feb. 2017; 89, 3959-3965. (Year: 2017).*
Sanchez-Ramirez et al. Bioprocess Biosyst Eng; 2017 (online Aug. 2016): 40:9-22. (Year: 2017).*
Ferapontova et al. Chem. Commun.; 2010; 46: 1836-1838. (Year: 2010).*
Wang and Hutchins, Anal. Chem.; 1985; 57:1536-1541. (Year: 1985).*
Hart and Wring, Trends in analytical chemistry; 1997; 16; 2: 89-102. (Year: 1997).*
Sanchez-Ramirez et al. Bioprocess Biosyst Eng; 2017 (online Aug. 2016): 40:9-22. (Year: 2016).*
Ferapontova, E. et al., Electrochemical DNA sandwich assay with a lipase label for attomole detection of DNA, Chem. Commun. 46: 1836-1838, 2010.
Huang, C. et al., Long-range surface plasmon-enhanced fluorescence spectroscopy biosensor for ultrasensitive detection of *E. coli* O157:H7, Anal. Chem. 83: 674-7, 2011.
Hvastkovs, E. et al., Recent advances in electrochemical DNA hybridization sensors, Analyst, 135: 1817-29, 2010.
Lazcka, O. et al., Pathogen detection: a perspective of traditional methods and biosensors, Biosens. Bioelectron., 22: 1205-17, 2007.
Loaiza, O. et al., Disposable magnetic DNA sensors for the determination at the attomolar level of a specific enterobacteriaceae family gene. Anal. Chem., 80: 8239-45, 2008.
Munge, B. et al., Multiple enzyme layers on carbon nanotubes for electrochemical detection down to 80 DNA copies, Anal. Chem. 77: 4662-6. 2005.
Patolsky, F. et al., Detection of single-base DNA mutations by enzyme-amplified electronic transduction, Nat. Biotechnol., 19: 253-257, Mar. 2001.
Ramakers, C. et al., Assumption-free analysis of quantitative real-time polymerase chain reaction (PCR) data, Neuroscience Letters, 339: 62-66, 2003.
Sanderson, M. et al., Sensitivity of bacteriologic culture for detection of *Escherichia coli* O157: H7 in bovine feces, J. Clin. Microbiol., 33(10): 2616-9, 1995.
Schloter, M. et al., The use of immunological methods to detect and identify bacteria in the environment; Biotechnol. Adv., 13: 75-90, 1995.
Shipovskov, S. et al., Electrochemical sandwich assay for attomole analysis of DNA and RNA from beer spoilage bacteria Lactobacillus brevis, Biosensors and Bioelectronics, 34: 99-106, 2012.
Zhang, Y. et al., Detection of ~$10^3$ copies of DNA by an electrochemical enzyme-amplified sandwich assay with ambient $O_2$ as the substrate, Anal. Chem., 76: 4093-7. 2004.
Fapyane, D. et al., Electrochemical Assay for a Total Cellulase Activity with Improved Sensitivity, Analytical Chemistry, 89(7): 3959-2965, Feb. 28, 2017.

* cited by examiner

SEQUENCE LISTING

```
<160> NUMBER OF SEQ ID NOS: 7

<210> SEQ ID NO 1
<211> LENGTH: 28
<212> TYPE: DNA
<213> ORGANISM: Lactobacillus brevis

<400> SEQUENCE: 1 ttttttttt ggaagctcgt tcgactta                                    28

<210> SEQ ID NO 2
<211> LENGTH: 27
<212> TYPE: DNA
<213> ORGANISM: Lactobacillus brevis

<400> SEQUENCE: 2
aactcaccag ttcgccactt tttttt                                     27

<210> SEQ ID NO 3
<211> LENGTH: 52
<212> TYPE: DNA
<213> ORGANISM: Lactobacillus brevis

<400> SEQUENCE: 3
tgcaagtcga acgagcttcc gttgaatcga gtggcgaact ggtgagtaac ac        52

<210> SEQ ID NO 4
<211> LENGTH: 30
<212> TYPE: DNA
<213> ORGANISM: Lactobacillus brevis

<400> SEQUENCE: 4
```

```
gctttgaggt gcgtgtttgt gcctgtcctg                                          30

<210> SEQ ID NO 5
<211> LENGTH: 52
<212> TYPE: DNA
<213> ORGANISM: Artificial sequence
<220> FEATURE:
<223> OTHER INFORMATION: Arbitrary DNA control probe
<220> FEATURE:
<221> NAME/KEY: misc_feature
<222> LOCATION: (1)..(52)
<223> OTHER INFORMATION: Arbitrary DNA control probe

<400> SEQUENCE: 5
tttttttttt ctgggaggga gggagggcaa ttcgaagggg acacgaaaat tg                 52

<210> SEQ ID NO 6
<211> LENGTH: 47
<212> TYPE: DNA
<213> ORGANISM: Artificial sequence
<220> FEATURE:
<223> OTHER INFORMATION: HER2-neu DNA aptamer
<220> FEATURE:
<221> NAME/KEY: misc_feature
<222> LOCATION: (1)..(47)
<223> OTHER INFORMATION: HER2-neu DNA aptamer

<400> SEQUENCE: 6
gcagcggtgt gggggcagcg gtgtgggggc agcggtgtgg ggttttt                      47

<210> SEQ ID NO 7
<211> LENGTH: 78
<212> TYPE: DNA
<213> ORGANISM: Artificial sequence
<220> FEATURE:
<223> OTHER INFORMATION: E-coli OMP DNA aptamer
<220> FEATURE:
<221> NAME/KEY: misc_feature
<222> LOCATION: (1)..(78)
<223> OTHER INFORMATION: E-coli OMP DNA aptamer

<400> SEQUENCE: 7
tttttatccg tcacacctgc tctacggcgc tcccaacagg cctctcctta cggcatatta         60
tggtgttggc tcccgtat                                                       78
```

METHOD AND ELECTRONIC DEVICE FOR DETERMINING THE CONCENTRATION OF AN ANALYTE

REFERENCE TO RELATED APPLICATION

This application claims priority from European Patent Application No. 1779278.1, filed Jul. 3, 2017, the entire content of which is incorporated herein by reference.

FIELD OF THE INVENTION

The present invention relates to a method for determining the concentration of an analyte in a sample, said method comprising contacting said sample with a solution comprising magnetic beads, a capture probe, a reporter probe and cellulase, wherein the MB-analyte-reporter-cellulase sandwich leads to degradation of an insulating layer surrounding an electrode thereby causing a change in electrical properties at the electrode surface, wherein said change in electrical properties is a function of the amount of analyte in said sample.

BACKGROUND OF THE INVENTION

Sensitive and specific assaying of nucleic acids, proteins, and whole cells is crucial in cancer and bacterial disease diagnostics and treatment and is of major significance for identification or biological pathogens, microbiome analysis, and analysis of genetically modified organisms. In practice, optical detection methods (such as polymerase chain reaction PCR (Ramakers, C. et al, Assumption-free analysis of quantitative real-time polymerase chain reaction (PCR) data, Neurosci Lett. 339 (2003) p. 62-66) and ELISA (Schloter, M. et al., Assmus, B., Hartmann, A. The use of immunological methods to detect and identify bacteria in the environment. Biotechnol. Adv., 13 (1995) p. 75-90) and radioisotope labelling are most widely used for genetic and protein analysis, and time-consuming microbiological tools for whole cell growth and their microscopy analysis (Sanderson, M. et al. Sensitivity of bacteriologic culture for detection of *Escherichia coli* O157: H7 in bovine feces, J. Clin. Microbiol. 33 (1995) p. 2616-9). Therewith, practically required concentrations to be detected, when no time-consuming amplification schemes are used, are below pM levels and 100 cells per Litre. The assay should be also highly selective, fast, cost-effective, and, desirably, simple to be used by the minimally trained personal.

The required high selectivity of such analysis is provided by biorecognition molecules, such as nucleic acids, aptamers and antibodies, while new technologies and methodologies are sought to achieve high sensitivity as well as speed and cost of an assay. E.g. routinely used sandwich schemes with oxidoreductase enzyme labels and optical read-out of the enzymatically formed products, such as ELISA, may often not provide sufficient sensitivity of analysis; they use quite expensive enzyme labels and enzyme substrates, such as horseradish peroxidase or alkaline phosphatase and their substrate dyes. Other, more sensitive schemes imply either a sufficiently expensive design of the assay or/and insufficient storage stability, inappropriate for industrial production and routine use for ultrasensitive multiplex analysis of DNA/RNA, protein and cells in food, drink, and clinical samples and environmental and hospital bacterial contamination (water, soil, air etc).

Currently, as alternative to optical assays, SPR (Huang, C.-J. et al. Long-range surface plasmon-enhanced fluorescence spectroscopy biosensor for ultrasensitive detection of *E. coli* O157:H7, Anal. Chem. 83 (2011) 674-7) and electrochemistry (Hvastkovs, E. G. et al, Recent advances iia electrochemical DNA hybridization sensors, Analyst 135 (2010) 1817-29; Lazcka, O. et al. Pathogen detection: a perspective of traditional methods and biosensors, Biosens. Bioelectron. 22 (2007) 1205-17) are intensively used for assaying of nucleic acids, proteins and cells. Sensitive, accurate and inexpensive electrochemical approaches are most promising for practical applications, due to possibility of rapid detection with lower costs, smaller equipment size and lower power requirements, and easy adaptation for in-field analysis by minimally trained personal. Combined with catalytic signal amplification strategies, electrochemical biosensors demonstrate detection limits as low as femtomolar NA and pmolar protein sensing. Combination of a bilirubin oxidase label and redox polymer allowed analysis of $10^3$ copies of DNA hybridized in a sandwich construction (Zhang, Y. et al, Detection of ~$10^3$ copies of DNA by an electrochemical enzyme-amplified sandwich assay with ambient $O_2$ as the substrate, Anal. Chem, 76 (2004), p. 4093-7). In an electrochemical ELISA with peroxidase and alkaline phosphatase as indicators, 10 fmol $ml^{-1}$ DNA was detected (Patolsky, F. et al. Detection of single-base DNA mutations by enzyme-amplified electronic transduction, Nat. Biotechnol. 19 (2001), p. 253-7), further methodological improvement allowed to reach attomole detection limits (Munge, B. et al. Multiple enzyme layers on carbon nanotubes for electrochemical detection down to 80 DNA copies, Anal. Chem. 77 (2005), p. 4662-6).

Currently, electrochemical approaches that combine oxidoreductase-based signal amplification with a sandwich hybridization strategy allow fM-aM analysis of DNA, which is comparable to PCR-based assays. Such sensitivity of the enzyme-amplified DNA sandwich assays was demonstrated, however, mostly with short synthetic DNA sequences, and only few electrochemical assays were able to detect long naturally occurring DNA or RNA. Protein and cell analysis often suffers from the electrode surface fouling by interfering competitive species present in the real samples such as blood/serum proteins.

To achieve high sensitivity and specificity of real sample analysis sandwich assays using magnetic beads and labelled with e.g. oxidoreductases (Munge, B. et al. Multiple enzyme layers on carbon nanotubes for electrochemical detection down to 80 DNA copies, Anal. Chem. 77 (2005) p. 4662-6; Loaiza, Ó. A. et al, Disposable magnetic DNA sensors for the determination at the attomolar level of a specific; enterobacteriaceae family gene, Anal. Chem. 80 (2008) 8239-45), hydrolases such as lipase have been developed (Shipovskov S. et al. Electrochemical sandwich assay for attomole analysis of DNA and RNA from beer spoilage bacteria *Lactobacillus brevis*, Biosens, Bioelectron. 34 (2012) p. 99-106). However, such assays generally suffer from expensive labels, low stability, and/or expensive electrode modifications. For example, the combination of lipase and synthetic redox-active thiolated ester as a lipase substrate immobilized on gold electrodes resulted in a sensitive assay, but the costs of the synthetic ester and the low stability of the substrate layer on electrodes were unsatisfactory for industrial applications (Ferapontova E. et al. Electrochemical DNA sandwich assay with a lipase label for attomole detection of DNA, Chem. Commun. 46 (2010) p. 1836-1838). Most of currently existing MB sandwich assays has restricted commercial applicability; they may be insufficiently robust due to the electrode reproducibility issues, and the redox enzyme-substrate couples and electrode materials are expensive, giving only a modest profit in price compared to the optical assays. Therefore, there is a need for a method to determine the presence of analytes in a sample, wherein the method employs a stable assay which at the same time is cost effective, has a high sensitivity and specificity and is easy to use.

SUMMARY OF THE INVENTION

The inventor of the present invention has developed a cost effective and highly sensitive method for detection of analytes such as for example nucleic acids, proteins and cells. In this method, cellulase is used as an enzymatic label that degrades a cellulose layer surrounding an electrode thereby causing a change m the electrical signal at the electrode surface.

Accordingly, one aspect of the present invention relates to a method for determining, the presence and/or the concentration of an analyte in a sample, said method comprising:
contacting said sample with a solution comprising:
    magnetic beads
    a capture probe capable of binding said analyte
    a reporter probe
    cellulase
    whereby, it the analyte is present, an MB-analyte-reporter-cellulase sandwich is formed;
contacting said solution comprising said sandwich with an electrode covered with an electrically insulating layer comprising or consisting of cellulose and/or a cellulose derivative
wherein the MB-analyte-reporter-cellulase sandwich leads to degradation of the insulating layer thereby causing a measurable change in electrical properties at the electrode surface, wherein said change in electrical properties is a function of the amount of analyte in said sample.

In one embodiment cellulase is added to the solution after addition of the magnetic beads, the capture probe and the reporter probe, such that, if the analyte is present, an MB-analyte-reporter complex is formed before addition of cellulase.

In a preferred embodiment said reporter probe is added to the solution after addition of the magnetic beads and the capture probe, such that, if the analyte is present, an MB-analyte complex is formed before addition of reporter probe.

In one embodiment a step of isolating said MB-analyte complexes, MB-analyte-reporter complexes or MB-analyte-reporter-cellulase sandwiches from the sample using a magnet.

The analyte may for example be an oligonucleotide, a protein or a cell.

In one embodiment the magnetic beads are chemically modified with streptavidin, avidin, gold, biotin, or polymers such as dextrine and chitosan.

The capture probe can for example be an oligonucleotide, an antibody or an aptamer. In one embodiment said oligonucleotide is biotinylated. In an embodiment thereof, said oligonucleotide is biotinylated DNA.

The reporter probe can for example be an oligonucleotide, an antibody or an aptamer. In one embodiment said oligonucleotide is biotinylated. In an embodiment thereof, said oligonucleotide is biotinylated DNA.

In one preferred embodiment said cellulose is biotinylated or conjugated with streptavidin or avidin.

It is preferred that the insulating layer comprises or consists of nitrocellulose.

Another aspect of the present invention relates to a device for measuring the concentration of an analyte, wherein said device comprises an electrode covered with an electrically insulating layer comprising or consisting of cellulose or cellulose derivatives, wherein said electrode is embedded in a solution comprising magnetic beads, a capture probe and a reporter probe, wherein addition of analyte and cellulose to said solution leads to the formation of a sandwich leading to a cellulose mediated degradation of the nitrocellulose layer thereby causing a measurable change in electrical properties at the electrode surface, wherein said change in electrical properties is a function of the amount of analyte in said sample.

In one embodiment said solution further comprises cellulose. The analyte is as described elsewhere herein. Also, the capture probe, the reporter probe and the insulating layer are as described elsewhere herein. Thus, preferably, said insulating layer comprises or consists of nitrocellulose.

Yet another aspect of the present invention relates to a biosensor comprising the device according to the present invention.

A further aspect of the present invention relates to a kit comprising an electrode covered with an electrically insulating layer comprising or consisting of cellulose or cellulose derivatives, magnetic beads, a capture probe, a reporter probe and cellulase.

The analyte is a described elsewhere herein. Also, the capture probe, the reporter probe and the insulating layer are, as described elsewhere herein. Thus, preferably, said insulating layer comprises or consists of nitrocellulose.

BRIEF DESCRIPTION OF THE DRAWINGS

FIG. 10A) OMP5-OMP5 (1), OMP3-OMP3 (2), OMP5-Ab (3), OMP3-Ab (4), arbitrary DNA-arbitrary DNA (5), arbitrary DNA-Ab (6), Ab-Ab (7), Ab-OMP5 (8), Ab-OMP3 (9); FIG. 10B) OMP5-OMP5 (1), OMP3-OMP3 (2), OMP5-Ab (3), OMP3-Ab (4), arbitrary DNA-arbitrary DNA (5), arbitrary DNA-Ab (6), Ab-Ab (7), Ab-OMP5 (8), Ab-OMP3 (9), FIG. 10C) OMP5-OMP5 (1), OMP5-Ab (2), Ab-Ab (3), arbitrary DNA-arbitrary DNA (4), Ab-OMP5 (5), Ab-OMP3 (6), arbitrary DNA-Ab (7); FIG. 10D) OMP5-OMP5 (1), ONIP5-Ab (2), Ab-Ab (3), Ab-OMP5 (4), Ab-OMP3 (5), arbitrary DNA-Ab (6), arbitrary DNA-arbitrary DNA (7), Potential scan rate is 0.1 V s$^{-1}$. Data reflect faradaic and capacitive approaches, correspondingly.

DETAILED DESCRIPTION OF THE INVENTION

Definitions

Figure 1:
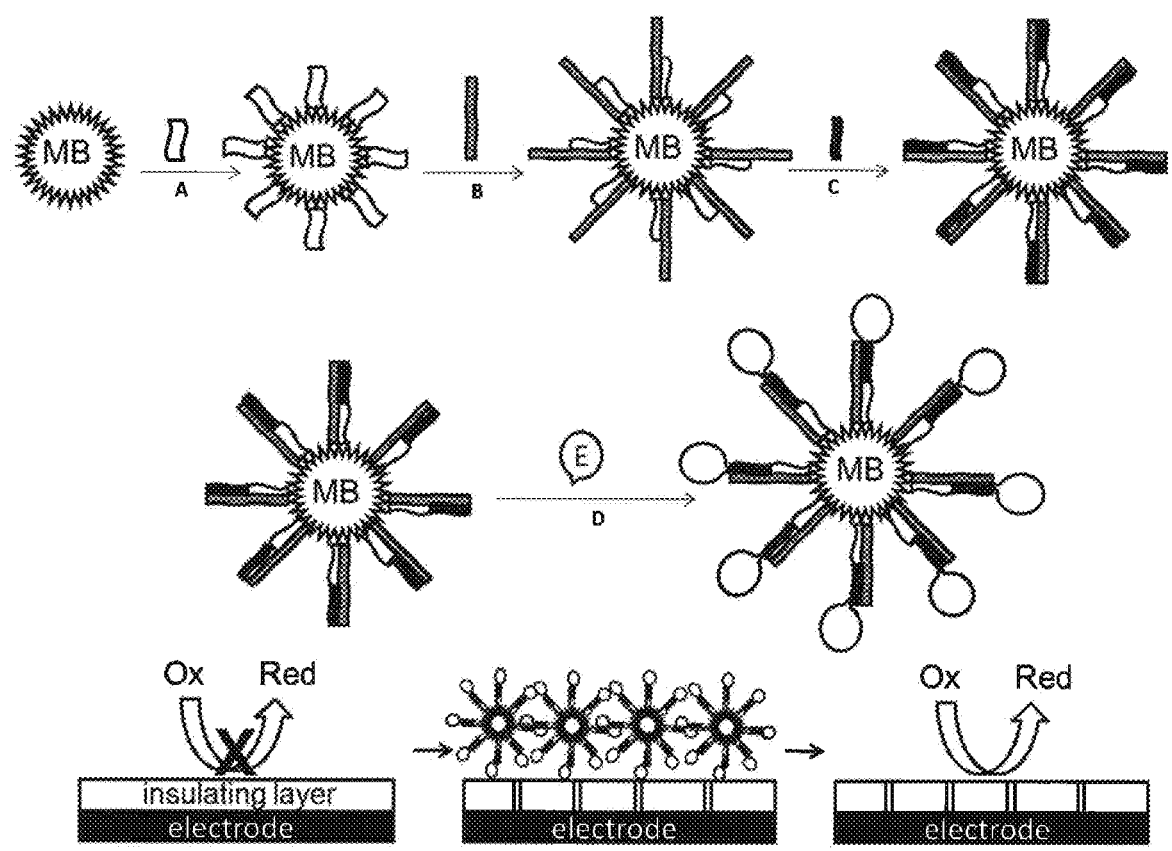
FIG. 1. Schematic presentation of a sandwich assay on magnetic heads (MB) with cellulose as a label: sandwich assembly on magnetic beads, labelling of the sandwich with cellulase label, and application of magnetic beads to the electrode covered with insulating. (nitro)cellulose film. If the targeted analyte molecule is present, the full sandwich assembly is labelled with cellulose, which then interacts with the substrate film making it less insulating/more permeable for redox reaction to occur on the electrode surface. With this, the faradaic signal produced is measured as a function of the analyte concentration. Alternatively, ro redox probe is present in solution, and only capacitive signal is electrochemically detected and calibrated vs, the analyte concentration. A—Biotinylated capture DNA, aptamer, antibody; B—Targeted DNA, RNA, protein, cell; C—biotinylated reporter DNA, aptamer, antibody; D—Avidin-cellulase conjugate, streptavidin-biotinylated cellulose conjugate.

The term "nucleotide" as used herein defines a monomer of RNA or DNA. A nucleotide is a nucleobase to which a phosphate group is attached through a ribose or a deoxyribose ring. Mono-, di-, and tri-phosphate nucleosides are referred to as nucleotides.

The term "oligonucleotide" as used herein refers to oligonucleotides of both natural and/or non-natural nucleotides, including any combination thereof. The natural and/or non-natural nucleotides may be linked by natural phosphodiester bonds or by non-natural bonds. Preferred oligonucleotides comprise only natural nucleotides linked by phosphodiester bonds. The oligomer or polymer sequences of the present invention are formed from the chemical or enzymatic addition of monomer subunits. The term "oligonucleotide" as used herein includes linear oligomers of natural or modified monomers or linkages, including deoxyribonucleotides, fluorinated deoxyribonucleotides, ribonucleotides, anomeric forms thereof, peptide nucleic acid monomers (PNAs), locked nucleotide acid monomers (LNA), and the like, capable of specifically binding to a single stranded polynucleotide tag by way of a regular pattern of monomer-to-monomer interactions, such as Watson-Crick type of base pairing, base stacking, Hoogsteen or reverse Hoogsteen types of base pairing, or the like. Usually monomers are linked by phosphodiester bonds or analogs thereof to form oligonucleotides ranging in size from a few monomeric units, e.g. 3-4, to several tens of monomeric units, e.g. 40-60. Whenever an oligonucleotide is represented by a sequence of letters, such as "ATGCCTG," it will be understood that the nucleotides are in 5'→3' order from left to right and the "A" denotes deoxyadenosine, "C" denotes deoxycytidine, "G" denotes deoxyguanosine, and "T" denotes thymidine, unless otherwise noted. When a double stranded DNA molecule is shown, the nucleotides of the top strand are in 5'→3' order from left to right and the nucleotides of the bottom strand are then in 3'5' order from left to right. Usually, oligonucleotides of the invention comprise the four natural nucleotides; however, they may also comprise methylated or non-natural nucleotide analogs.

As used herein, "nucleic acid" or "nucleic acid molecule" refers to polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g. alpha-enantiomeric forms of naturally-occurring nucleotides), or a combination of both.

Modified nucleotides can have alterations in sugar moieties and/or in pyrimidine purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid molecule" also includes e.g. so-called "peptide nucleic acids," which comprise naturally-occurring or modified nucleic acid bases attached to a polyimide backbone. Nucleic acids can be either single stranded or double stranded. In an aspect of the present invention, 'nucleic acid' is meant to comprise antisense oligonucleotides (ASO), small inhibitory RNAs (siRNA), short hairpin RNA (shRNA) and micro NA (miRNA).

Method

One aspect of the present invention relates to a method for determining the presence and/or the concentration of an analyte in a sample, said method comprising:
contacting said sample with a solution comprising:
  magnetic beads (MB)
  a capture probe capable of binding said analyte
  a reporter probe
  cellulase
  whereby, if the analyte is present, an MB-analyte-reporter-cellulase sandwich construct is formed;
contacting said solution comprising said sandwich construct with an electrode covered with an electrically insulating layer comprising or consisting of cellulose and/or a cellulose derivative
wherein the MB-analyte-reporter-cellulase sandwich leads to degradation of the insulating layer thereby causing a measurable change in electrical properties at the electrode surface, wherein said change in electrical properties is a function of the amount of analyte in said sample.

It is appreciated that the sample, the magnetic beads, the capture probe, the reporter probe and the cellulase are added to the solution in any order.

One embodiment thereof relates to a method for determining the presence and/or the concentration of an analyte in a sample, said method comprising:
contacting said sample with said solution comprising:
  magnetic beads
  a capture probe capable of binding the magnetic beads and the analyte
  a reporter probe
  whereby, if the analyte is present, an MB-analyte-reporter complex is formed
contacting said MB-analyte-reporter complex with cellulase to provide an MB-analyte-reporter-cellulase sandwich
contacting said sandwich with an electrode covered with an electrically insulating layer comprising or consisting of cellulose and/or a cellulose derivative
wherein the MB-analyte-reporter-cellulase sandwich leads to degradation of the insulating layer thereby causing a measurable change in electrical properties at the electrode surface, wherein said change in electrical properties is a function of the amount of analyte in said sample.

Another embodiment thereof relates to a method for determining the presence and/or the concentration of an analyte in a sample, said method comprising:
contacting said sample with a solution comprising magnetic beads comprising a capture probe capable of binding said analyte
whereby the analyte, if present, is bound to the capture probe leading to the formation of an MB-analyte complex
binding a reporter probe to said. MB-analyte complex, whereby an MB-analyte-reporter complex is formed
contacting said MB-analyte-reporter complex with cellulase to provide an MB-analyte-reporter-cellulase sandwich
contacting said sandwich with an electrode covered with an electrically insulating layer comprising, or consisting of cellulose and/or a cellulose derivative
wherein the MB-analyte-reporter-cellulase sandwich leads to degradation of the insulating layer thereby causing a measurable change in electrical properties at the electrode surface, wherein said change in electrical properties is a function of the amount of analyte in said sample.

The method of the present invention may in a preferred embodiment further comprise a step of isolating said MB analyte complexes, MB-analyte-reporter complexes or MB-analyte-reporter-enzyme sandwich from the sample using a magnet. Thereby, the sandwich will be isolated from unbound components before it is exposed to the electrode.

Magnetic Beads and Capture Probe

In the method of the present invention, magnetic beads are used to capture the analyte. The analyte is bound to the magnetic beads via the capture probe. In one embodiment the capture probe is bound to the magnetic beads before binding of the analyte to the capture probe. Alternatively, the capture probe is bound to the analyte before binding to the magnetic beads.

In one embodiment the magnetic beads are at most 3 micrometer (μM) in diameter. More preferably, the magnetic beads are at most 2 μM in diameter, such as at most 1 μM in diameter. The diameter of the magnetic beads is for example in the range of from 0.1 μM to 3 μM, or such as from 0.5 μM to 3 μM.

The magnetic beads are in one preferred embodiment chemically modified to allow attachment of the capture probe to the magnetic beads. When the beads are chemically modified with a component, said component mill be present on the surface of the magnetic beads. Thus, the magnetic beads are preferably coated with said component.

Thus, in one embodiment the magnetic beads are chemically modified with streptavidin, gold or biotin. That is, the magnetic beads can be coated with streptavidin, avidin, gold, biotin, or polymers such as dextrane and chitosan.

In another embodiment the magnetic beads are chemically modified with polymers comprising COOH— and/or OH— groups. The magnetic beads may also be chemically modified with COOH— and/or OH-functionalised thiol linkers. Chemical modification of COOH— and/or OH— groups with amine-functionalized capture probes is preferably done by succinimide ester and carbodiimide coupling.

In another embodiment the magnetic beads are chemically modified with polymers comprising amine groups. The magnetic beads may also be chemically modified with amine-functionalised thiol linkers, Chemical modification of amine groups on magnetic beads with amine-, COOH— or HS-functionalised capture probes is preferably done by homobifunctional crosslinkers such as gluteraldehyde or by heterobifunctional crosslinkers.

Magnetic beads modified with streptavidin are preferably used for attachment of biotinylated capture probes, whereas magnetic beads modified with biotin are preferably used for attachment of streptavidin-conjugated capture probes. Magnetic beads modified with gold are preferably used for attachment of thiolated capture probes. COOH— and/or OH— modified magnetic heads are preferably used for attachment of amine-functionalised capture probes.

The capture probe is a component that is used to capture the analyte. The capture probe is capable of binding both to the magnetic beads and the analyte. The capture probe is bound or attached to the magnetic beads, preferably via the chemical modification as discussed above.

The capture probe can for example be an oligonucleotide, an antibody or an aptamer.

In one embodiment the capture probe is an oligonucleotide. In one preferred embodiment the capture probe is a biotinylated oligonucleotide. In another preferred embodiment the capture probe is a thiolated oligonucleotide. In a further embodiment the capture probe is an oligonucleotide comprising an amine. The biotin-group, thiol-group or amine-group is normally linked to the 3'-end or the 5'-end of the oligonucleotide.

The oligonucleotide can be DNA or RNA or modifications thereof. Thus, in one embodiment the capture probe comprises or consists of DNA and/or modified DNA. In another embodiment the capture probe comprises or consists of RNA and/or modified RNA. In a particular embodiment the capture probe is biotinylated DNA.

In another embodiment the capture probe is an antibody. The antibody is capable of binding the analyte. Thus, preferably, the antibody is specific for the analyte.

In yet another embodiment the capture probe is an aptamer. The term "aptamer" as used herein means an oligonucleotide or a peptide that binds to the analyte.

Oligonucleotide aptamers are nucleic acid species that have been engineered through repeated rounds of in vitro selection or equivalently, SELEX (systematic evolution of ligands by exponential enrichment) to bind to various molecular targets such as small molecules, proteins, nucleic acids, and even cells, tissues and organisms. Aptamers are useful in biotechnological and therapeutic applications as they offer molecular recognition properties that rival that of the commonly used biomolecule, antibodies. Further, aptamers may offer advantages over antibodies as they can be engineered completely in a test tube, are readily produced by chemical synthesis, possess desirable storage properties, and elicit little or no immunogenicity in therapeutic applications.

Peptide aptamers are polypeptides selected or engineered to bind the analyte. Preferably, peptide aptamers comprise or consist of one or more peptide loops of variable sequence displayed by a protein scaffold. They are typically isolated from combinatorial libraries and often subsequently improved by directed mutation or rounds of variable region mutagenesis and selection.

The variable regions are preferably synthesized as part of the same polypeptide chain as the scaffold and are constrained at their N and C termini by linkage to it. This double structural constraint decreases the diversity of the conformations that the variable regions can adopt, and this reduction in conformational diversity lowers the entropic cost of molecular binding when interaction with the target causes the variable regions to adopt a single conformation. As a consequence, peptide aptamers can bind their targets tightly, with binding affinities comparable to those of antibodies.

Peptide aptamer selection can be made using different systems, but the most used is currently the yeast two-hybrid system. Peptide aptamers can also be selected from combinatorial peptide libraries constructed by phage display and other surface display technologies such as mRNA display, ribosome display, bacterial display and yeast display. These experimental procedures are also known as biopannings. Among peptides obtained from biopannings, mimotopes can be considered as a kind of peptide aptamers. Peptides panned from combinatorial peptide libraries can be found in the database MimoDB.

The solution comprising magnetic beads comprising a capture probe is preferably a buffer, such as for example phosphate-buffered solution (PBS). In one embodiment the solution has a pH in the range of from 6 to 8, such as pH in the range of from 6.5 to 7.5. In a preferred embodiment the solution has pH 7.

Analyte

The term "analyte" as used herein is a component, substance or chemical species of interest. It is the presence of the analyte that is to be determined by the method of the present invention.

The analyte can for example be a biomarker. A biomarker is normally a protein or a nucleic acid that can be used to assess the biological state and/or the condition of an individual. The detection of a biomarker can for example be used to determine whether an individual has a specific disease or disorder. In one embodiment the individual is a human.

In one embodiment the analyte is selected from the group consisting of nucleic acids, proteins and cells.

In one embodiment the analyte is an oligonucleotide or a nucleic acid. The terms "oligonucleotide" and "nucleic acid" are defined above. The analyte can for example be DNA or RNA. The RNA may for example be selected from the group consisting of messenger RNA (mRNA), ribosomal RNA (rRNA), transfer RNA (tRNA), small nuclear RNA (snRNA), micro RNA (miRNA), small interfering RNA (siRNA), short hairpin RNA (shRNA).

In another embodiment said analyte is a protein or a peptide. The protein may for example be a biomarker or a cancer biomarker such as for example human epidermal growth factor receptor 2 (HER2), HER2 is also known as HER2/neu or HER2-neu. HER2 is a member of the human epidermal growth factor receptor (HER/EGFR/ERBB) fa ily Overexpression of HER2 has been shown to be indicative of certain aggressive types of breast cancer.

The method of the present invention can also be used to determine the presence or the concentration of cells. Thus, in yet another embodiment the analyte is a cell.

Thus, method can be used to determine whether an individual is infected with a specific microorganisms and/or bacteria or whether food, water and/or soil is/are contaminated with microorganisins and/or bacteria.

Thus, in one embodiment the analyte is a bacterial cell. In one embodiment the bacteria is a gram positive bacteria. In another embodiment the bacteria is a gram negative bacteria. In one embodiment, the bacterial cell is a pathogenic bacterial cell. Pathogenic bacteria are bacteria that can cause infection. The pathogenic bacteria or pathogenic bacterial cells may for example be selected from the group consisting of *Streptococcus, Staphylococcus, Escherichia, Shigella, Salmonella, Neisseria, Brucella, Mycobacterium, Nocartha, Listeria, Francisella, Legionella, Borrelia, Chlamydia, Helicobacter, Pseudomonas* and *Yersinia*.

In one embodiment the bacteria is *Escherichla coli* (*E. coli*).

Sample

The sample is mixed with the capture probe or the magnetic beads comprising the capture probe. If the analyte is present in the sample, it will bind to the capture probe which bind to or is bound to the magnetic beads.

In one embodiment the sample is obtained from a human or an animal. Its one embodiment the animal is a domestic animal. Domestic animal for example includes, dogs, cats, cattle, sheep, pigs, horses, donkeys, ducks, chickens, gooses and rabbits In another embodiment the animal is a mammal.

The sample can be a body fluid sampic, sueh as a blood sample, a urine sample, a faecal sample, gastric juice, a serum sample or a saliva sample. The sample may also be obtained by a skin, swabs, nasal swabs or cheek epithelium swabs. In one embodiment the sample is a skin biopsy er a lymph node biopsy.

The method of the present invention may also be used for determining whether food water is contaminated, for example with microorganisms such as bacteria. Thus, in another embodiment the sample is a food sample or a water sample.

Reporter Probe

The reporter probe is capable of binding to the analyte.

The reporter probe can for example be an oligonucleotide, an antibody or an aptamer.

In one embodiment the reporter probe is an oligonucleotide. In one preferred embodiment the reporter probe is a biotinylated oligonucleotide. The biotin-group is normally linked to the 3'-end or the 5'-end of the oligonucleotide.

The oligonucleotide can be DNA or RNA or modifications thereof. Thus, in one embodiment the reporter probe comprises or consists of DNA and/or modified DNA. In another embodiment the reporter probe comprises or consists of RNA and/or modified RNA. In a particular preferred embodiment the reporter probe is biotinylated DNA.

In another embodiment the reporter probe is an antibody. The antibody is capable of binding the analyte. Thus preferably, the antibody is specific for the analyte.

In yet another embodiment the reporter probe is an aptamer. The term "optamer" as used herein means an oligonucleotide or a peptide that bind to the analyte. The aptamer is as defined above for the capture probe.

Cellulase

The method of the present invention uses cellulose as an enzymatic indicator in the electrochemical assay.

Cellulase hydrolyses cellulose in a complex several step reaction, by hydrolytic cleavage of ß-1-4-glycosidic bonds of the polymer. Thereby, the cellulose degrades the cellulose insulating layer surrounding or covering the electrodes thereby generating a shift in the electrical signal. The shift or the change in electrical properties is a function of the amount of analyte in said sample.

In a preferred embodiment the cellulose is biotinylated or conjugated with streptavidin or avidin. Thus, the cellulose binds to the reporter probe preferably via biotin, streptavidin or avidin.

For example, the reporter probe can be biotinylated and the cellulose conjugated with streptavidin. Thereby, the reporter probe is bound to the cellulose via a biotin-streptavidin linkage. In another embodiment the cellulose is conjugated with biotin and the reporter molecule is conjugated with biotin. Cellulose is then linked to a reporter molecule by the addition of streptavidin thereby creating a biotin-streptavidin-biotin linkage.

The cellulose can be any cellulose. Thus, the cellulose may origin from any organism. In one embodiment the cellulase is from *Aspergillus niger*.

The insulating layer surrounding the electrode comprises or consists of cellulose and/or a cellulose derivative. It is appreciated that the cellulose derivative can be degraded by cellulase.

The insulating layer may for example comprise or consist of a polymer comprising cellulose and/or a water insoluble cellulose derivative such as nitrocellulose or ethyl cellulose or ethyl hydroxyethyl cellulose.

In a preferred embodiment said insulating layer comprises or consists of nitrocellulose and/or a nitrocellulose derivative.

Cellulose layer is electrically insulating and prevent any electrochemical reaction of a soluble redox indicator at the cellulosemodified electrode interface. The contact of the cellulase-labelled MB-assembled sandwich with the cellulose-film-modified electrode results in the enzymatic digestion of the film. When the cellulose film on the electrode surface is digested by cellulose, it becomes less insulating, and the electrode surface thereby becomes more accessible for the electrode reactions. This can be followed electrochemically, with a redox agent such as for example ferricyanide. Thus, in one embodiment the solution comprising the sandwich and the electrode comprise a redox agent such as for example ferricyanide, ferrocene and ferrocene derivatives, catechol, or ruthenium hexamine.

The digestion of the film by cellulose leads to an increase in Faradic currents due to the redox indicator transformation that becomes possible on the surface of electrodes. Alternatively, since the conductive properties of the film are changed upon the film degradation by cellulase, the capacitive currents recorded at the electrodes also increase, Both Faradaic and capacitive changes directly correlate with the amount of cellulose on the electrode surface and, thus, with the number of the analyte molecules captured on MB. The electrochemical signals are thus proportional to the concentration of the captured analyte molecules and by this means they can be identified. By following the electrochemical signal, both detection and quantification of the analyte molecules is achieved.

Electrochemical Cell

The electrical signal is measured by using an electrochemical cell. Electrochemical cells for use in accordance with the invention may be constructed according to conventional methods known in the art (A. J. Bard and L. F. Faulkner, Electrochemical Methods. Fundamentals and Applications, John Wiley & Sons, 2001).

The electrochemical cell may for example comprise at least two electrodes or at least three electrodes. In one embodiment the electrochemical cell comprises two electrodes, in a preferred embodiment the electrochemical cell comprises three electrodes.

Typically, the electrochemical cell may be constructed comprising a Working electrode, a counter electrode (also referred to as an auxiliary electrode) and a reference electrode immersed in the same electrolyte solution or in different electrolyte solutions. Thus, the working and counter electrodes are in electrical contact with the reference electrode either by immersing the electrodes in the same electrolyte solution or by immersing the working and counter electrodes in an electrolyte solution which is electrically linked to the reference electrode electrolyte by a salt-bridge or a semi-peri teable membrane.

The working electrode, as referred to herein, is the electrode comprising the insulating cellulose layer. When the cellulose layer is degraded and the electrode surface becomes exposed to the electrolyte solution an electrical signal is generated.

The reference electrode can be any commonly used reference electrode such as for example a hydrogen electrode, a calomel electrode or copper/copper(II) sulfate electrode. In a preferred embodiment the reference electrode is a silverlsilver chloride electrode. The counter electrode can be any commonly used counter electrodes such as for example platinum, stainless steel, carbon electrodes, in a preferred embodiment the counter electrode is either a Pt electrode or a stainless steel electrode.

The electrochemical cell may also be constructed comprising only a working and a counter electrode immersed in the same electrolyte solution or in different electrolyte solutions separated by a semipermeable membrane. The auxiliary electrode functions as a cathode whenever the working electrode is operating; as an anode and vice versa. The potential of the auxiliary electrode is usually not measured and is adjusted so as to balance the reaction occurring at the working electrode, Auxiliary electrodes are often fabricated from electrochemically inert materials such as gold, platinum, or carbon.

The electrically conducting surface of the electrode according to the present invention may for example comprise or consist of carbon or graphite. In one embodiment said electrically conducting surface comprises or consists of a material selected from the group consisting of spectroscopic graphite, highly oriented pyrolytic graphite, graphene oxide, reduced graphcne, mesoporous carbon, carbon microfiber, carbon fiber, carbon paste, carbon cloth, screen-printed carbon, carbon nanomaterials and carbon paper. Other electrodes such as any metal or indium oxide, or metal oxide based electrodes may also be used.

The electrolyte solution comprises charge carriers that are ions or molecules. The charge carriers may be selected from the group consisting of protons, hydroxide ions, metal ions, halide ions, ammonium ions and oxyanions. Oxyanions may include nitrate ions, sulphate ions and phosphate ions. In a preferred embodiment the electrolyte solution is a salt water solution. For example, the electrolyte may comprise NaCl.

The electrolyte solution may further comprise a pH buffer such as for example HEPES, PBS or Tris. Preferably, the electrolyte solution has a pH at which the enzymes adsorbed at the electrode of the invention are stable and active. Preferably the electrolyte solution is maintained at a pH of between 5 and 10 and more preferably between 7 and 8.

In one embodiment the electrolyte solution comprises $K_3[Fe(CN)_6]$ as a redox agent. In a more specific embodiment the solution comprises 1 mM $K_3[Fe(CN)_6]$ in 0.1 M PBS, pH 5.

In the electrolytic cell as described herein the current flowing with the working electrode at a given potential relative to the reference electrode, may be used as a quantitative measure of the amount of oxidized or reduced redox agent present in the electrolyte. The current flowing in the electrochemical cell can be related to the concentration of the oxidized or reduced form of the redox agent present in the electrolyte through equations which are well known in the art.

The electrochemical cell can for example function as a voltammetric transducer where cell current is recorded as a function of the applied potential thereby generating a voltammogram. The current flowing in the electrochemical cell can be related to the concentration of the oxidized or reduced form of the redox agent present in the electrolyte through equations which are well known in the art. The electrochemical cell may for example employ cyclic voltammetry, differential pulse voltammetry, square wave voltammetry, impedance spectroscopy, chronoamperometry, or chronocoulometry. In another embodiment the electrochemical cell employs cyclic voltammetry and chronocoulometry. In a preferred embodiment the electrochemical cell employs cyclic voltammetry, chronocoulometry and/or electrochemical impedance spectroscopy A Device Another aspect of the present invention relates to a device for measuring the concentration of an analyte, wherein said device comprises an electrode covered with an electrically insulating layer comprising or consisting of cellulose or cellulose derivatives, wherein said electrode is embedded in a solution comprising magnetic heads, a capture probe and a reporter probe, wherein addition of analyte and cellulase to said solution leads to the formation of a sandwich leading to a cellulase mediated degradation of the nitrocellulose layer thereby causing a measurable change in electrical properties at the electrode surface, wherein said change in electrical properties is a function of the amount of analyte in said sample.

The electrode can constitute either a part of the compact electrochemical cell, in which the cellulase-labelled sandwich assembly on magnetic beads is directly placed on the electrode surface, or a fluidic device, in which addition of the analyte and/or other reagents, their reactions on magnetic beads, and their delivery to the cellulose-modified electrode are performed through the channels of the compact fluidic or microfluidic cartridges. The cell is preferably connected to the electrochemical analyser. Thus, in one embodiment the device is a fluidic device.

In one embodiment the solution further comprises cellulose.

The analyte is as defined herein above.

The magnetic beads are as described herein above. Thus, the magnetic beads are in one preferred embodiment chemically modified to allow attachment of the capture probe to the magnetic beads. In one embodiment, the solution comprises magnetic beads, which are bound to the capture probe.

The capture probe is as defined herein above.

The reporter probe is as defined herein above.

The insulating layer is as defined herein above. Thus, in a preferred embodiment, said insulating layer comprises or consists of nitrocellulose.

A further aspect of the present invention relates to a biosensor comprising the fluidic device as described herein.

Kit

Yet another aspect of the present invention relates to a kit comprising an electrode covered with an electrically insulating layer comprising or consisting of cellulose or cellulose derivatives, magnetic beads, a capture probe, a reporter probe and cellulose.

The analyte is as defined herein above.

The magnetic beads are as described herein above. Thus, the magnetic beads are in one preferred embodiment chemically modified to allow attachment of the capture probe to the magnetic beads. In one embodiment, the solution comprises magnetic beads, which are bound to the capture probe.

The capture probe is as defined herein above.

The reporter probe is as defined herein above.

The insulating layer is as defined herein above. Thus, in a preferred embodiment, said insulating layer comprises or consists of nitrocellulose.

EXAMPLES

Methods

Biotinylation of Cellulase

Conjugation of cellulase to biotin was performed by reacting 100 µl of 20 mg ml-1 cellulase reacted with 10 µl of 5 mg ml-1 biotin-amido-hexanoic acid 3-sulfo-N-hydroxysuccinimide ester (BAC-sulfoNHS) in 10 mM phosphate buffer saline pH 7.4 (PBSal) with gentle stirring for 30 minutes at RT. Then, the mixture was applied to column and spin at 700 g for 2 minutes.

Graphite Electrode Modification

Graphite (Gr) electrode having a diameter of 3.05 mm and a geometrical surface area of 0.071 cm$^2$ was polished with silicon carbide emery paper for 30 s, and subsequently polished on A4 paper (Papyrus AB, Mölndal, Sweden) for 30 s to yield flat surface. A 10 µl of 0.5% nitrocellulose solution (4% nitrocellulose in ethanol/diethyl ether as a stock solution) was casted on the electrode surface and dried, under the argon flow. As alternative electrodes, screen printed carbon, carbon paper electrodes and/or carbon electrodes printed on plastic can be used.

Electrochemical Detection

Cyclic voltammetry (CV), chronocoulometry (CA) and electrochemical impedance spectroscopy (EIS) were recorded using nitrocellulose modified Gr electrodes before and after exposure to the cellulase-labelled sandwich on magnetic beads, measurements were performed in a standard three-electrode electrochemical cell connected to a µAutolab potentiostat (Type III, Eco Chemie B.V., Utrecht, Netherlands) supported with GPES (version 4.9) and NOVA (Type 1.8.17) software. An Ag/AgCl (KCl$_{sat}$) electrode and a Pt wire were the reference and auxiliary electrodes, correspondingly. All electrochemical measurements were carried at 20±1° C. CV was recorded in 1 mM K$_3$[Fe(CN)$_6$] in 0.1 M PBS, pH 5 Faradaic and capacitive charges were evaluated from the CV data; the Faradaic charges—by integrating the ferricyanide reduction peak area, and the capacitive charges—by integrating the current-potential dependence in the region where no Faradic reaction occurred (a so-called capacitive area), within the −0.1 to +0.1 V potential window. The total charge consumed in the electrochemical reaction of ferricyanide (Q$_{faradaic}$) allows a more precise and sensitive analysis, since it takes into account the overall peak area (current integrated over time), In the assay development, the Q$_{faradaic}$ values plotted vs either the time or amount of target which is correlated with the amount of cellulase attached to the sandwich. Sandwich assembly was also correlated with the changes of the capacitive charge, Q$_{capacitive}$, stemming from the changes in the electric double layer capacitance, due to the structural changes of the nitrocellulose films exposed to cellulases. The EIS measurement was recorded in 1 mM K$_4$[Fe(CN)$_6$] and 1 mM K$_3$ [Fe(CN)$_6$] in 0.1 M PBS, pH 5, at applied frequencies 0.1-10$^5$ Hz and at a potential 0.2 V.

Electrochemical Detection of *L. brevis* DNA and RNA, HER2-neu and *E. coli* Cells A 5 µl (6.7 µl in the case of cells) of cellulase-sandwich assay mixture in 0.1 M PBS, pH 5, was applied to the nitrocellulose modified Or electrode and allowed to react for 45 minutes. Then, the Gr electrode was washed thoroughly with water and electrochemically interrogated.

Cell Growth and Sample Preparation

A 1 ml acoli in glycerol stock was mixed with 50 ml LB broth. The mixture was kept in the waterbath set at 37° C. for 24-48 h until the optical density (OD) reached 0.8. Based on McFarland Scale, OD=1 is equal to 3×108 CFU/ml.

Example 1

Nucleic Acid Analysis

Reporter probe and capture DNA sequences were selected and designed to hind short synthetic, DNA sequences specific for *Lactobacillus brevis* (*L. brevis*). The capture probe used has the nucleotide sequence SEQ ID NO:1 and was labelled at the 5' end with biotin resulting in the following capture probe: 5'-Biotin-(CH$_2$)$_6$-TTT TTT TTT TGG AAG CTC GTT CGA CTT A-3'.

The reporter probe used has the nucleotide sequence SEQ ID NO:2 and was labelled at the 3' end with biotin resulting in the following reporter probe: 5'-AAC TCA CCA GTT CGC The DNA sandwich was assembled on MBs, labelled with cellulase from *Aspergillus niger* (1 U mg$^{-1}$), and applied onto the surface of nitrocellulose-modified graphite (Gr) electrodes.

The DNA sandwich hybridization assembly was performed on streptavidin-coated MB (M-280 streptavidin, 10 mg ml$^{-1}$ with binding capability 200 pmol of ss-DNA per mg, or 20 pmol biotinylated antibody) allowed to react stepwise with the biotinylated capture DNA sequence, the target sequence and the reporter probe. First, 100 µl (0.4 nmol DNA-binding capacity) of MB were washed and decanted with a magnet in 3×100 µl of 20 mM PBS, pH 7, containing 0.15 M NaCl and 0.1% Tween 20, and finally re-dissolved in 100 µl of PBS. Then, a two-fold excess of the capture DNA was added to the solution of MB beads (0.5 nmoles of MB-streptavidin binding sites: 1 nmoles of DNA) and let react for 40 min, after that capture DNA-modified MB were carefully washed from non-reacted DNA (in 3×100 µl PBS) and re-suspended in 100 µl PBS, containing 10 mM MgCl$_2$.

Selection, amplification, and purification of DNA sequences specific for *L. brevis* were done according to previous reports (Shipovskoy S. et al. Electrochemical sandwich assay for attomole analysis of DNA and RNA from beer spoilage bacteria *Lactobacillus brevis*, Biosens. Bioelectron. 34 (2012) 99-106).

MB with 0.1 nanomoles (nmol) DNA-binding capacity were mixed with 1 amoles-100 picomoles (pmol) of synthetic DNA target, let to react for 40 mm washed, decanted and re-suspended in an equivalent amount of PBS-MgCl$_2$, let to react with 0.6 nmol of the reporter DNA.

The target complementary DNA (cDNA) has the nucleotide sequence SEQ ID NO:3, The target non-complementary DNA (ncDNA) has the nucleotide sequence SEQ ID NO 4.

As a control, an arbitrary DNA control probe having the sequence SEQ ID NO: 5 was used. The arbitrary DNA probe was biotinylated at the 3' end giving the following DNA control probe: NH$_2$—(CH$_2$)$_6$-TTT TTT TTT TCT GGG AGG GAG GGA. GGG CAA TTC GAA GGG GAC ACG AAA ATT G-Biotin.

The sandwich assembly (SA) was labelled with cellulase by addition of 10-fold mole excess of streptavidin (1 nmol, 40 min reaction time, then washing/decantation/re-suspension) and further addition of 4-fold excess of cellulase-biotin conjugate (0.4 nmol) to react with the biotinylated end of the reporter probe of the hybridised sandwich through the streptavidin linker. Finally, the MB/SA/cellulase was washed, decanted and re-suspended in 10 µl of 0.1 M PBS pH 5.

Figure 2A:
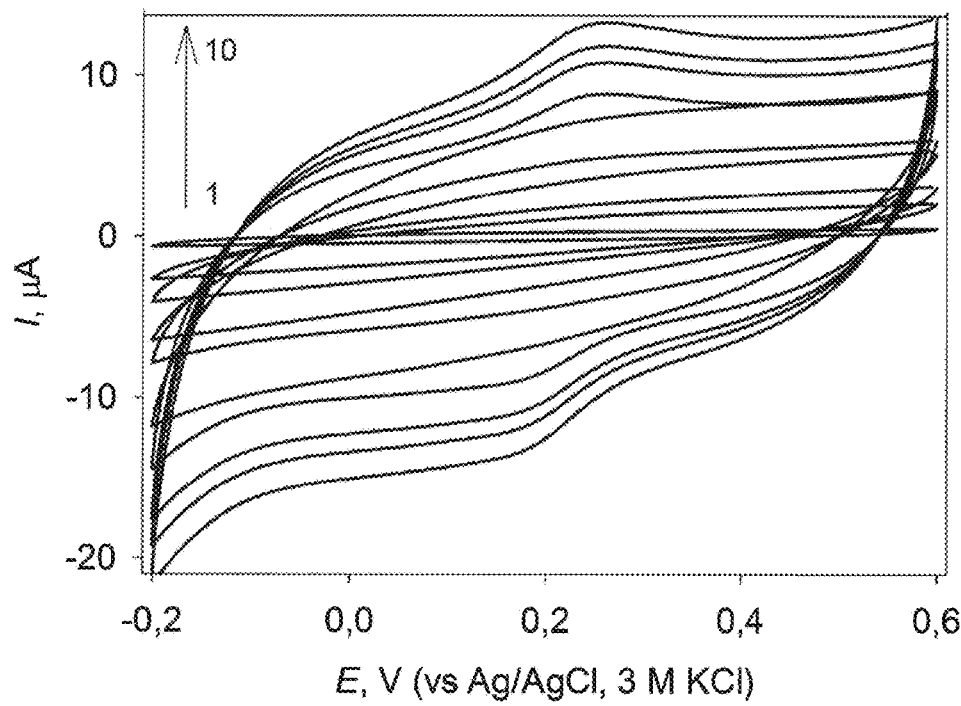
FIGS. 2A and 2B show representative cyclic voltammograms recorded with nitrocellulose-modified graphite electrodes in 0.1 molar (M) PBS, pH 5, in the presence (A) and absence (B) of 1 mM. $K_3[Fe(CN)_6]$ before (1) and after treatment with magnetic beads/DNA sandwich/cellulase assembly with synthetic *L. brevis* specific DNA, concentration range is between $10^{-5}$ and $10^2$ prnoles; reaction time is 45 minutes (min) (2-10). Potential scan rate $0.1$ V s$^{-1}$. Data reflect faradaic and capacitive approaches, correspondingly.
Figure 2B:
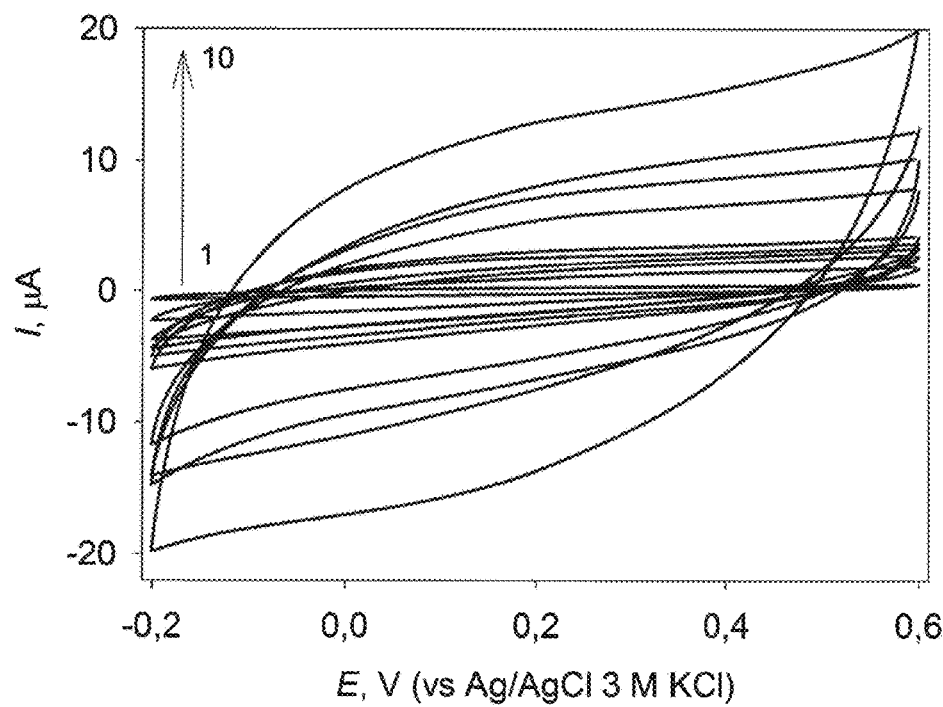

With increasing concentration of the DNA target sequence in solution the voltammetric signal from the ferricyanide redox agent, exhibited as an increase in the voltammetric current intensity (FIG. 2A), and the capacitive currents in the absence of ferricyanide (FIG. 2B) increased starting from 0.1 finale of DNA.

Figure 3A:
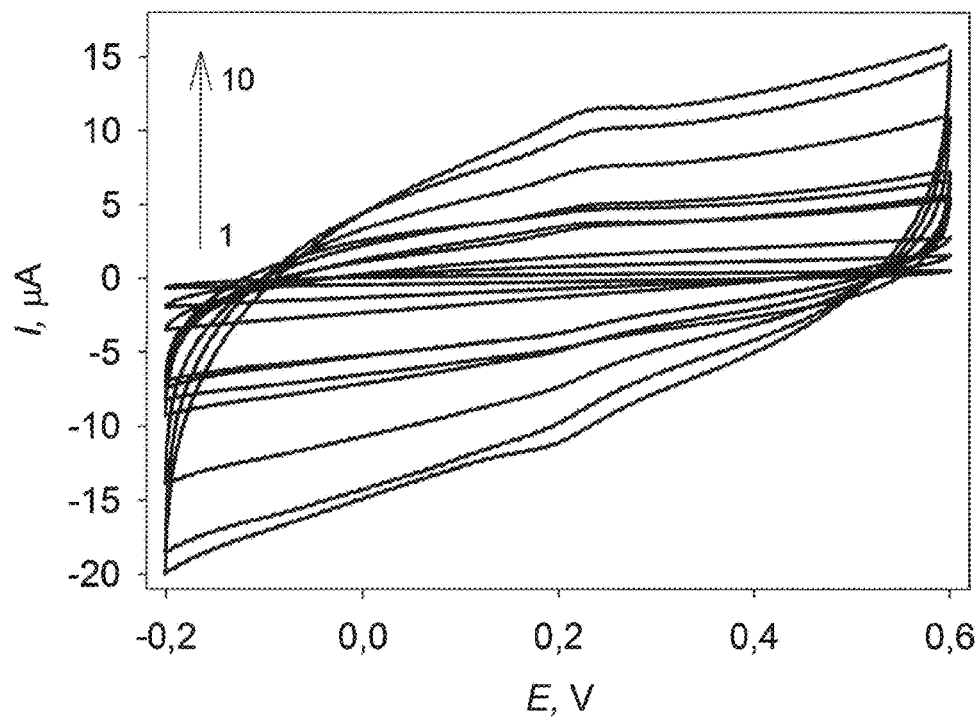
FIGS. 3A and 3B show representative cyclic voltammograms recorded with nitrocellulose-modified graphite electrodes in 0.1 M PBS, pH 5, in the presence (A) and absence (B) of 1 millimolar (mM) $K_3[Fe(CN)_6]$ before (1) and after treatment with magnetic beads/DNA sandwich/cellulase assembly with *L. brevis* ribosomal RNA, concentration range is between $10^{-5}$ and $10^2$ picomoles (pyrroles); reaction time is 45 min (2-10). Potential scan rate is 0.1 V s$^{-1}$. Data reflect faradaic and capacitive approaches, correspondingly.
Figure 3B:
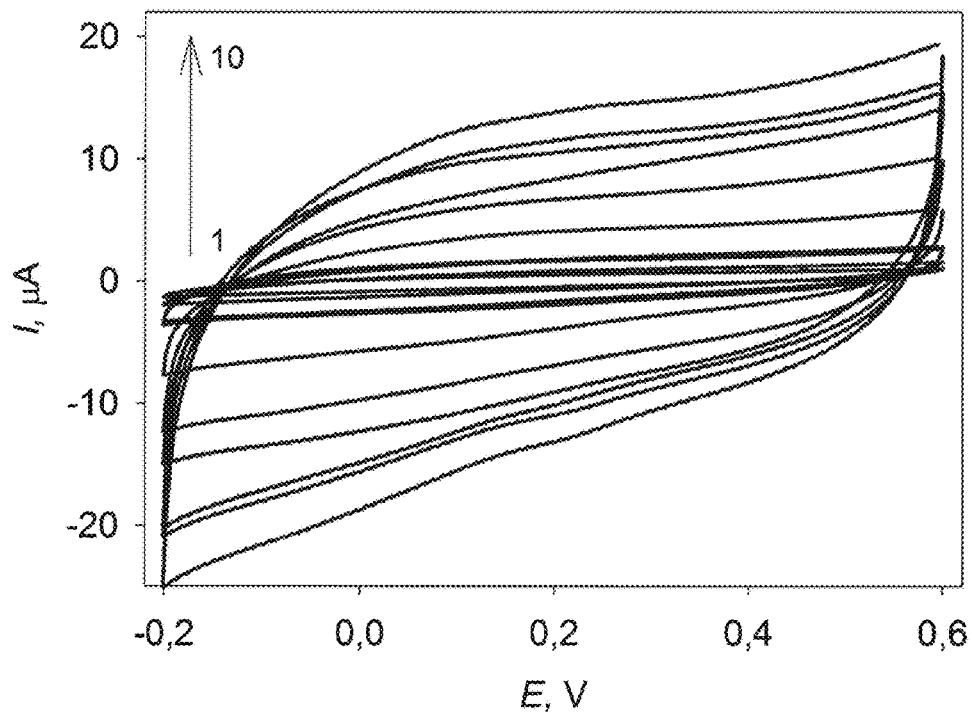

Similar pattern was observed with ribosomal RNA (rRNA) purified from *L. brevis* cells (FIGS. 3A and 3B): both Faradaic, and capacitive currents increase with increasing concentration of ribosomal RNA in samples. When rRNA was used as a target, MB with 0.1 nmol DNA-binding capacity were mixed with from 1 ample to 100 pmole rRNA, reacted for 40 min at 75° C., washed, decanted and re-suspended in PBS-MgCl$_2$, and reacted with 0.6 nmole of the reporter DNA.

Figure 4:
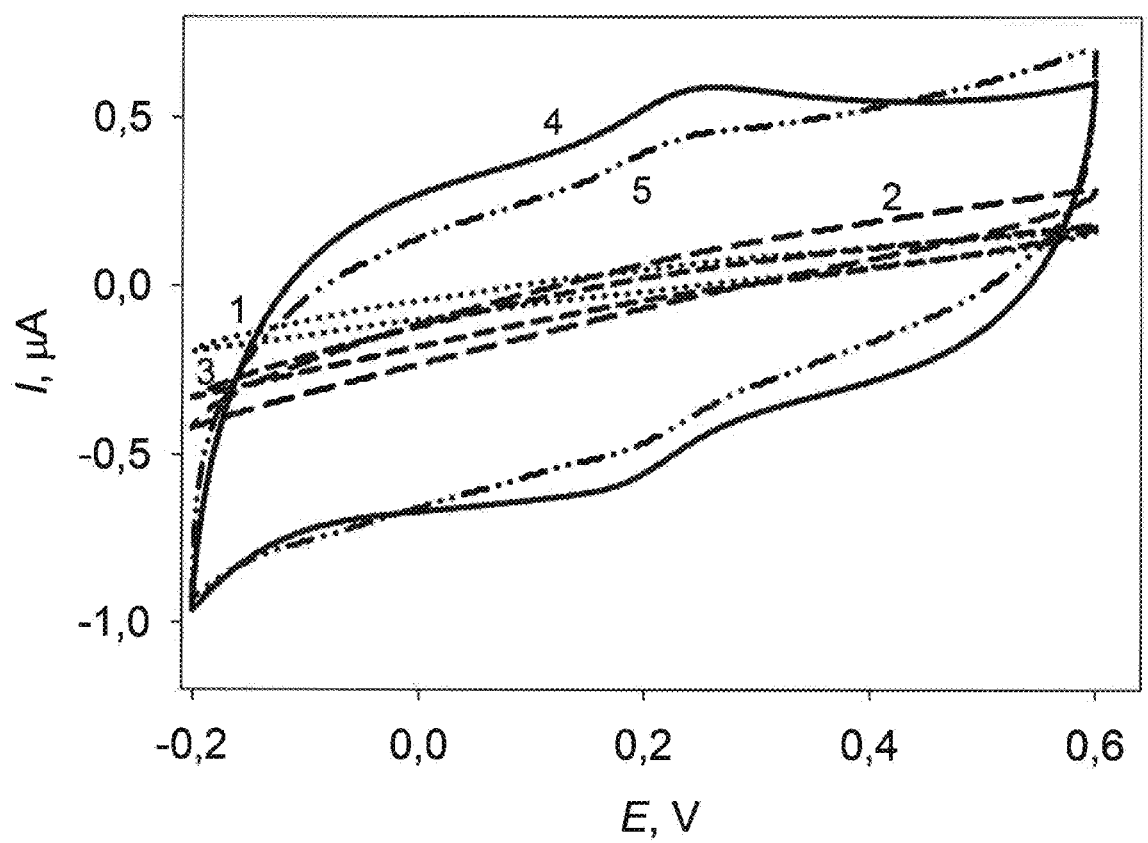
FIG. 4. Representative cyclic voltarmnograms recorded with a nitrocellulose-modified graphite electrode in 0.1 M PBS, pH 5, in the presence of 1 mM K$_3$[Fe(CN)$_6$] before (1) and after treatment with magnetic beads/DNA sandwich cellulase assembly with 100 attomole synthetic L. brevis specific DNA sequence (4), L. brevis ribosomal RNA (5), non-complementary DNA sequence (2) and E. coli ribosomal RNA (3). Potential scan rate is 0.1 V s$^{-1}$.
Figure 5:
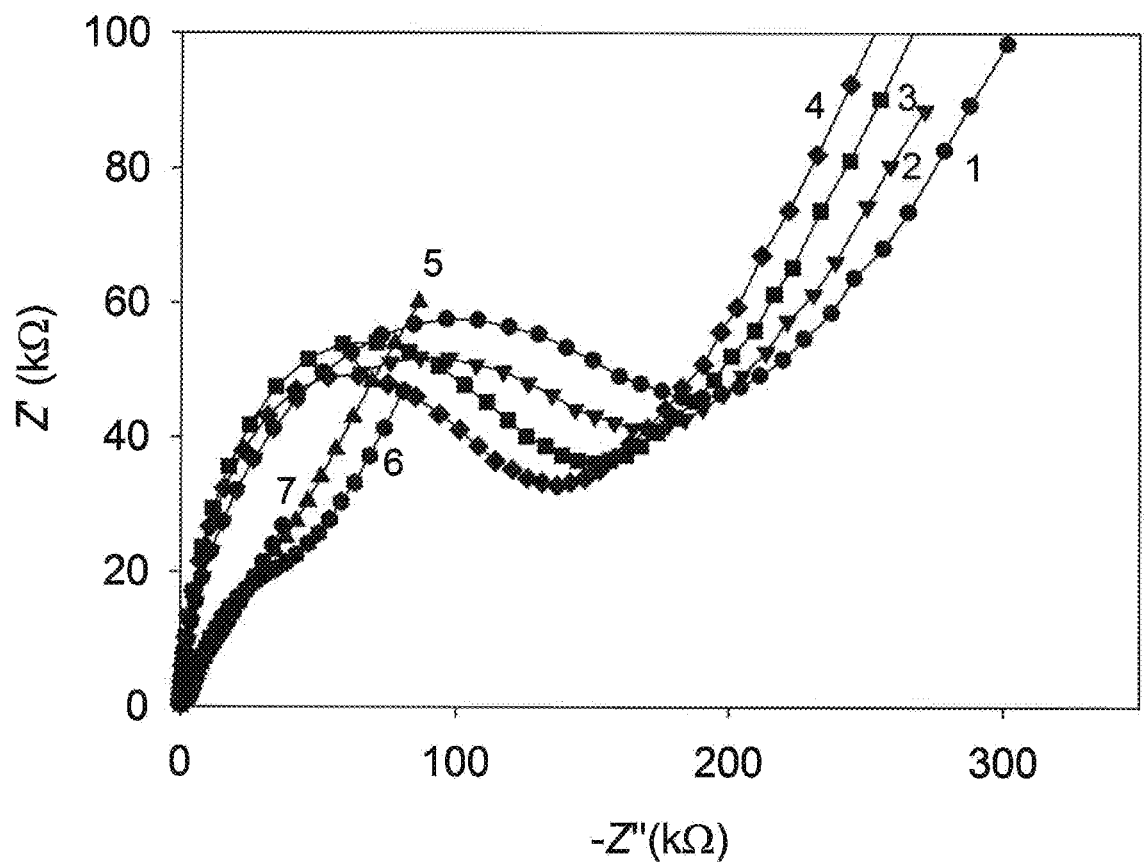
FIG. 5. Representative electrochemical impedance spectra (Nyquist plots) recorded in 0.1 M PBS, pH 5, containing 1 mM K$_4$[Fe(CN)$_6$] and K$_3$[Fe(CN)$_6$] with a nitrocellulose-modified graphite electrode treated with cellulase-labeled DNA sandwich assembled on MB with L. brevis DNA as a target; within concentration range of 0 (1), 10$^{-5}$ to 1 prole (2-7). Applied potential: 0.2 V; frequency range: from 0.1 to 10$^5$ Hz.

No significant changes neither in Faradaic nor in capacitive current was observed when MBs not labelled with cellulase were used, or when the DNA sandwich assay specific for *L. brevis* was performed with a DNA sequence non-complementary to the capture probe sequence or with *E. coli* rRNA (FIG. 4). More sensitive 10 attomole analysis of *L. brevis* DNA was achieved with electrochemical impedance spectroscopy appeared to be more sensitive to the changes in the insulating properties of the nitrocellulose films, with the impedimetric signal representing a charge transfer resistance semicircle correspondingly decreased with increasing concentration of the analyte (FIG. 5).

Figure 6A:
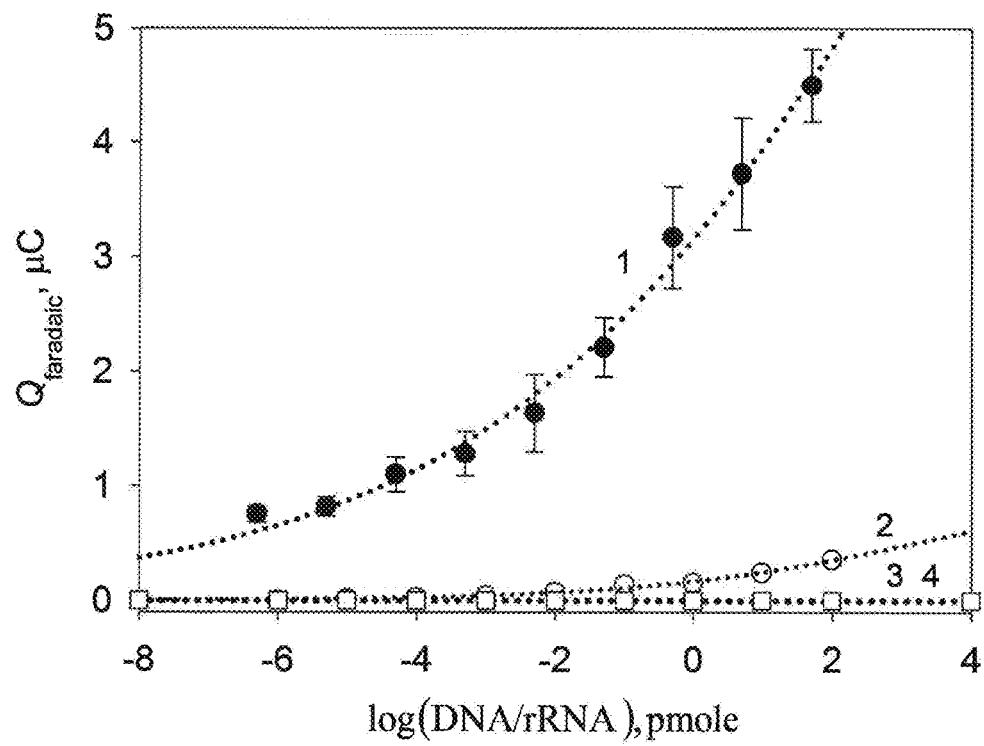
FIGS. 6A and 6B show dependence of the faradaic Q$_{faradaic}$ (FIG. 6A) and capacitive Q$_{capacitive}$ (FIG. 6B) charges on the log concentration of L. brevis synthetic DNA (1), L. brevis ribosomal RNA (2), non-complementary DNA (3) and E. coli ribosomal RNA (4), data derived from cyclic voltammetry data recorded with nitrocellulose-modified graphite electrodes in 0.1 M PBS, pH 5, in the presence (FIG. 6A) and absence (FIG. 6B) of 1 mM K$_3$[Fe(CN)$_6$] before and after treatment with magnetic beads/DNA sandwich/cellulase assembly; reaction time: 45 min. Potential scan rate 0.1 V s$^{-1}$. Data reflect faradaic and capacitive approaches, correspondingly.
Figure 6B:
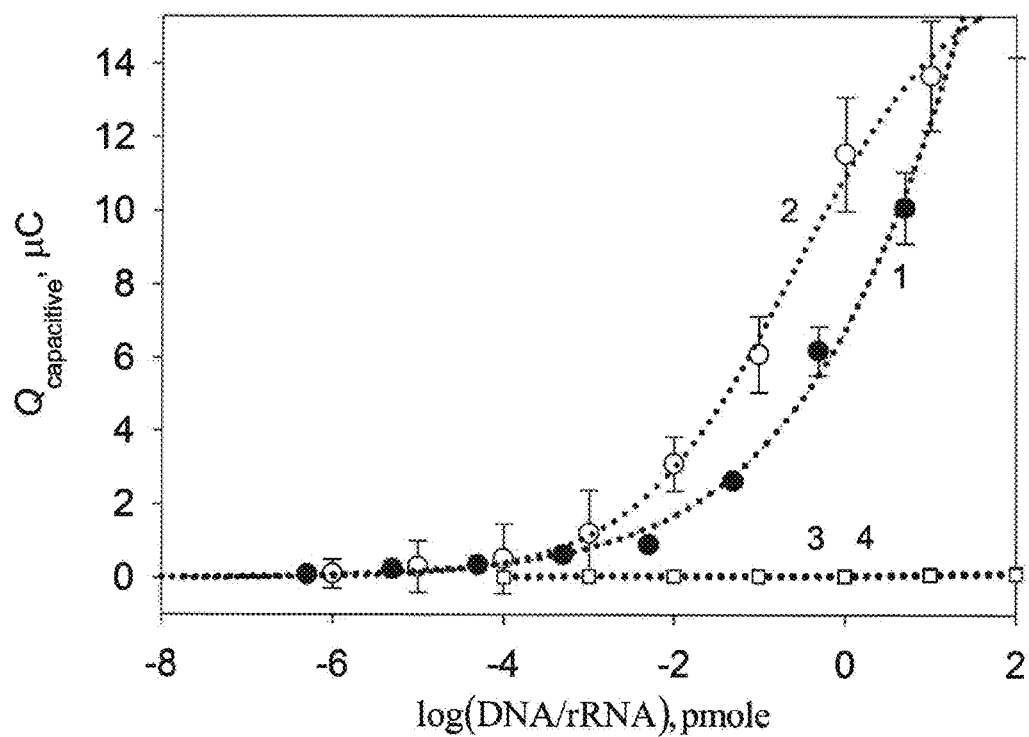
Figure 7A:
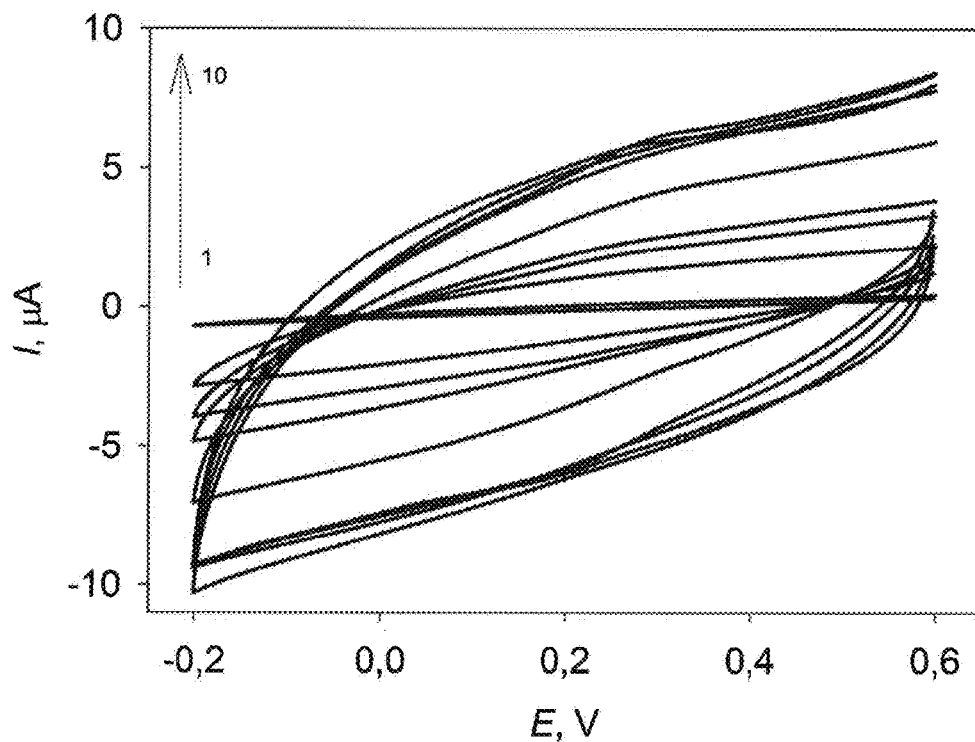
FIGS. 7A-7D show representative cyclic voltammograms recorded with nitrocellulose-modified graphite electrodes in 0.1 M PBS, pH 5, in the presence (FIG. 7A) and absence (FIG. 7B) of 1 mM K$_3$[Fe(CN)$_6$] before (1) and after treatment with magnetic beads/sandwich/cellulase assembly with HER2/neu protein, its concentration ranging between 10$^{-15}$-10$^{-8}$ M (2-10). Sandwich assay is performed with different combinations of capture-reporter molecules, (FIG. 7A) Ab-Ab, (FIG. 7B) Ab-aptamer, (FIG. 7C) aptainer-Ab, and (FIG. 7D) aptamer-Aptamer. Potential scan rate is 0.1 Vs$^{-1}$.
Figure 7B:
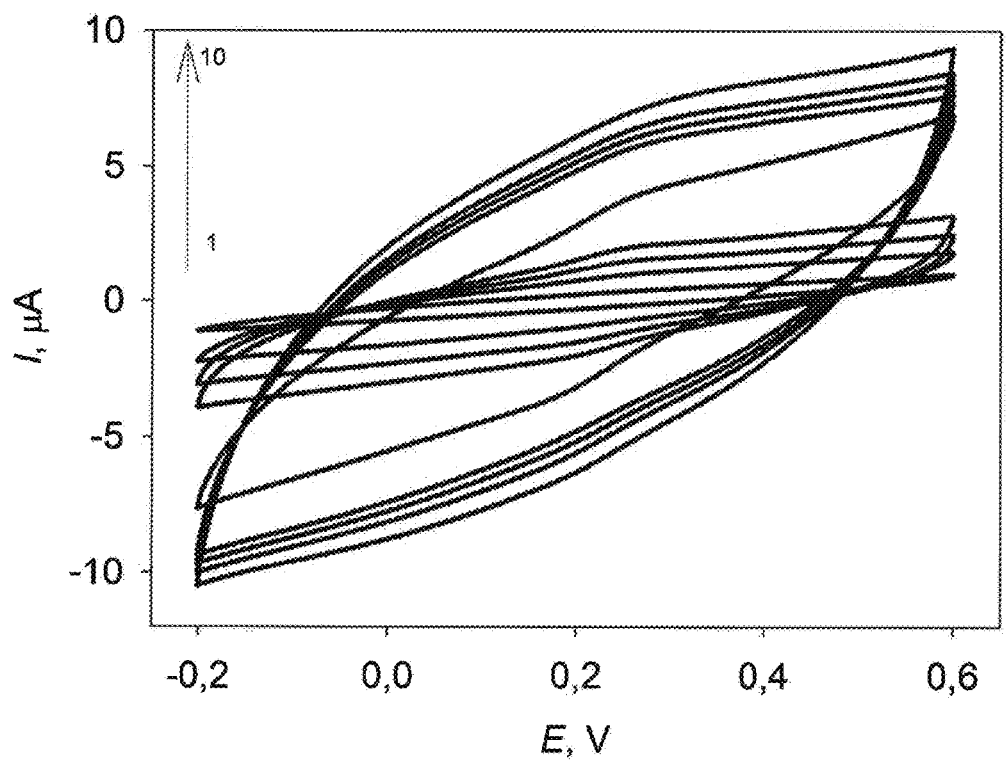
Figure 7C:
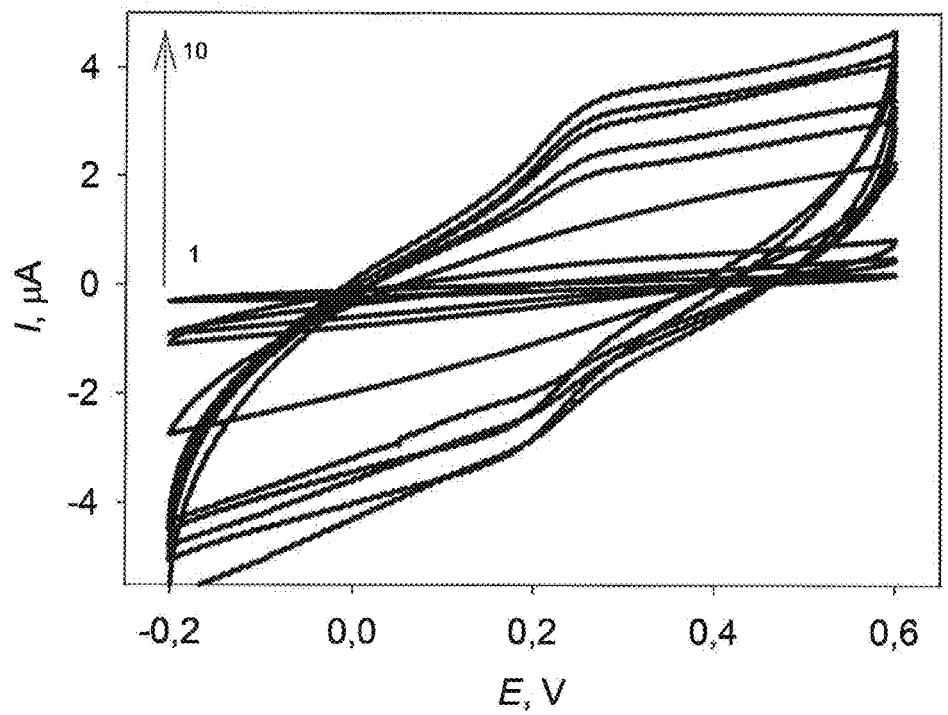
Figure 7D:
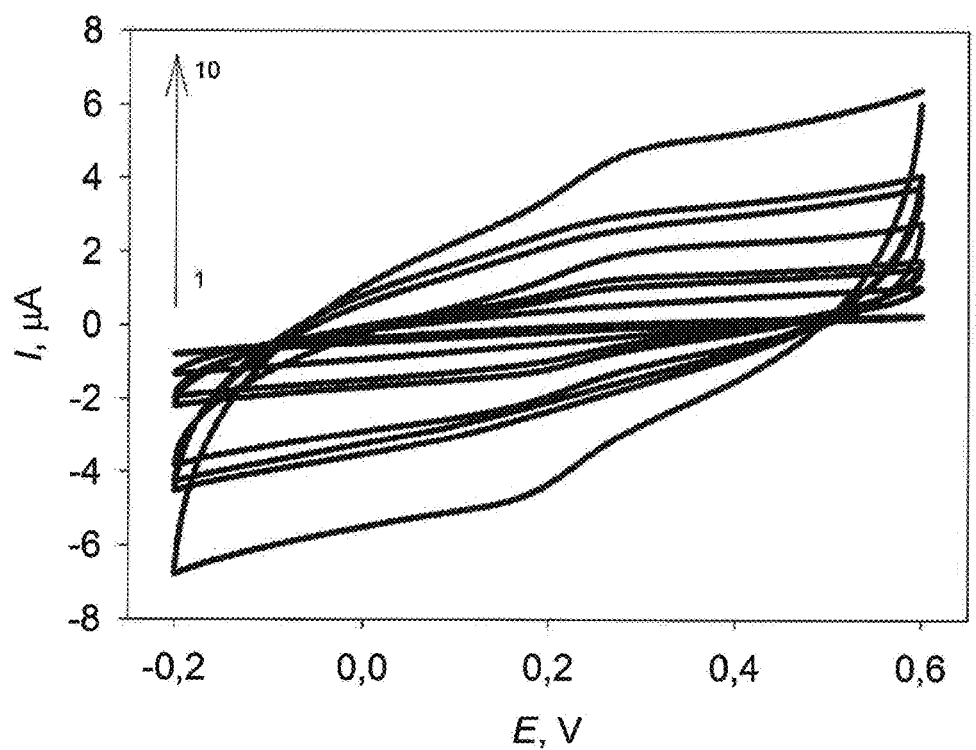

Both Faradaic Q$_{faradaic}$ and capacitive Q$_{capacitive}$ charges associated with voltammetric data were plotted versus the amount of the analysed DNA and RNA in the analysed solutions (FIGS. 6A and 6B). Q$_{faradaic}$ and Q$_{capacitive}$ were obtained by integrating the ferricyanide reduction peak area and current-potential dependences in the region where no Faradic reaction occurred (a so-called capacitive area), within the −0.1 to +0.1 V potential window. As can be seen, the Q$_{faradaic}$ signals appeared to be less sensitive to the changes in concentration of long bacterial ribosomal RNA, compared to short synthetic DNA sequences (FIG. 6A). The Q$_{capacitive}$, stemming from the changes in the electric double layer capacitance and resulting from the structural changes of the nitrocellulose films exposed to cellulases, appeared to show a very close sensitivity to both short synthetic DNA specific to *L. brevis* and long bacterial ribosomal RNA purified from *L. brevis* cells. No interference could be followed when short synthetic and bacterial nucleic sequences not specific to *L. brevis* were used for sandwich assembly (FIG. 6B).

Example 2

Protein Analysis

Cancer biomarker protein HER2-neu was captured on either antibody- or aptamer-modified MBs. The sandwich assembly was accomplished by further reaction of the MB-bound protein with either an aptamer or a biotinylated HER2/neu antibody (Ab). By this several different sandwich assemblies were studied: Ab/HER2-neu/Ab, Ab/HER2-neu/aptamer, aptamer/HER2-neu/Ab, and aptamer/HER2-neu/aptamer (FIGS. 7A-7D).

The HER2/neu aptamer has the sequence SEQ ID NO:6 and is coupled to biotin at the 5' end resulting in the following aptamer: Biotin-5'-GCA GCG GTG TGG GGG CAG CGG TGT GGG GGC AGC GGT GTG GGG TTT TT-3'.

Protein sandwich assembly (SA) on MBs was performed by reacting 250 µl of MBs M-280 (500 pmol ss-DNA or 50 pmol biotinylated antibody binding capability) with 1000 pmol HER2/neu aptamer or 100 pmol biotinylated HER2/neu antibody for 1 hour at room temperature (RT). Then, the MBs was washed three times and re-suspended in 250 µl of buffer (20 mM PBS pH 7 for MB/aptamer or PBS for MB/antibody), pmol of MB-aptamer or MB-antibody were reacted with 1 ml solution containing different HER2/neu protein concentration from $10^{-15}$-$10^{-8}$ for 1 hour at RT. Then, the MBs were washed three times and resuspended in 20 µl of buffer containing 25 pmol of aptamer or antibody for 1 hour at RT. The mixture was washed and resuspended with 20 µl of buffer and 25 pmol of streptavidin. The mixture was washed and resuspended with 20 µl of buffer followed by the addition of 25 pmol of biotinylated cellulose from *Aspergillus niger* (1 U mg$^{-1}$). Finally, the mixture was washed and resuspended in 20 µl of 0.1 M PBS, pH 5.

Figure 8A:
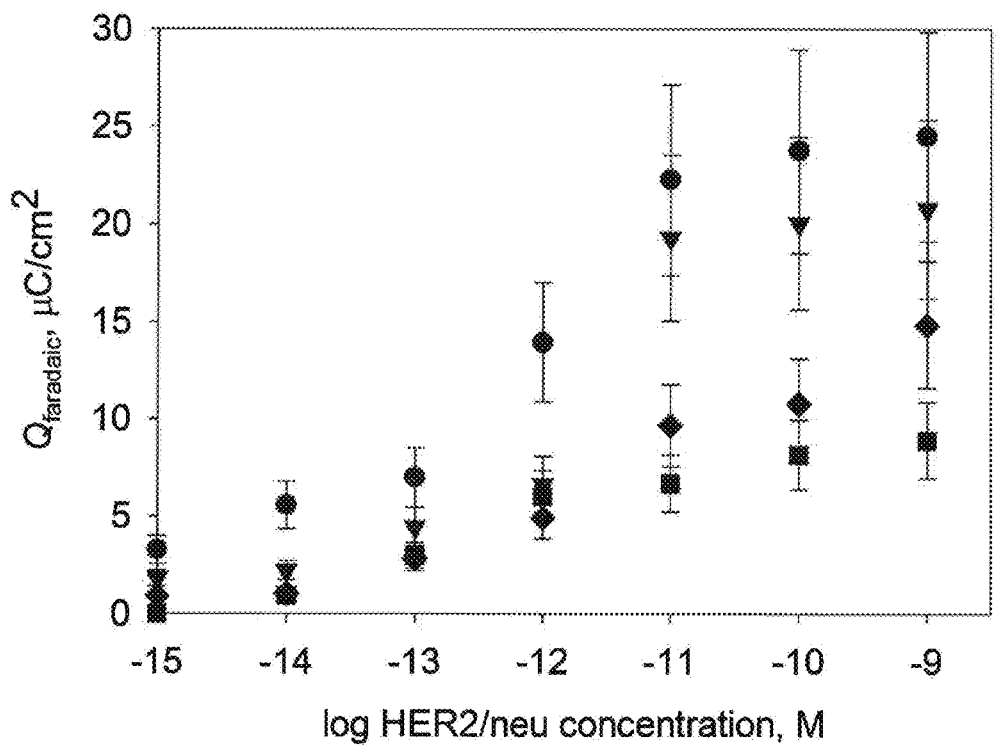
FIGS. 8A and 8B show dependence of the faradaic (FIG. 8A) and capacitive (FIG. 8B) charges on the log concentration of HER2/neu protein, data derived from the cyclic voltammvoltammograms recorded with nitrocellulose-modified graphite electrodes in 0.1 M PBS, pH 5, in the presence (FIG. 8A) and absence (FIG. 8B) of 1 mM K$_3$[Fe(CN)$_6$] before and after treatment with magnetic beads/sandwich/cellulose assembly with HER2/neu protein, Sandwich is assembled with different capture-reporter biomolecule combinations: Ab-Ab (circles), Ab-aptamer (triangles), aptarner-Ab (squares) and aptamer-aptamer (diamonds). Potential scan rate is 0.1 V s$^{-1}$. Data reflect faradaic and capacitive approaches, correspondingly.
Figure 8B:
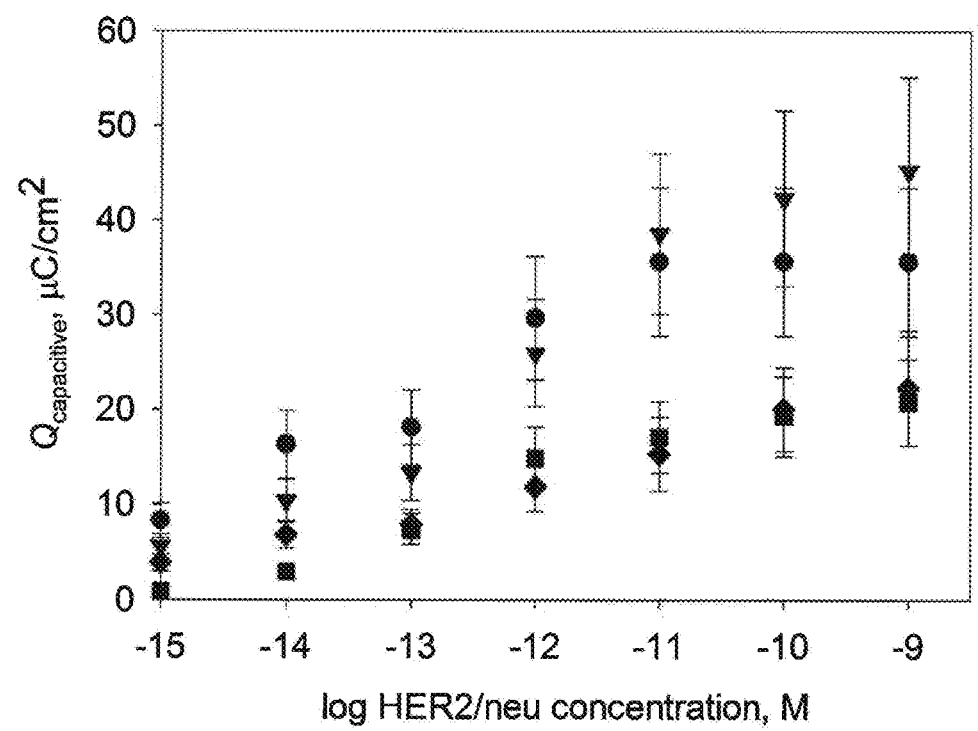

The ceilulase-labelled assemblies on MBs allowed 1 fmol/ml analysis of the HER2-neu protein, which cut-off concentration in blood is $10^{-1}$ M (10 fmole/ml). No interference from bovine serum albumin protein was observed, Both the Q$_{faradiac}$ and Q$_{capacitive}$ versus the protein concentration plots allowed sensitive analysis of the protein, though the capacitive analysis exhibited slightly better performance (FIG. 8A). Depending on the nature of the capture and reporter biomolecules (either Ab or aptamer), a quite different sensitivity of analysis was observed, with the best performance, with this particular protein and Ab/aptamers couples, achieved with MB/Ab/HER2-neu/Ab/cellulase and MB/Ab/HER2-neu/aptamer/cellulase constructions (FIG. 8B).

Example 3

Cell Analysis

Figure 9:
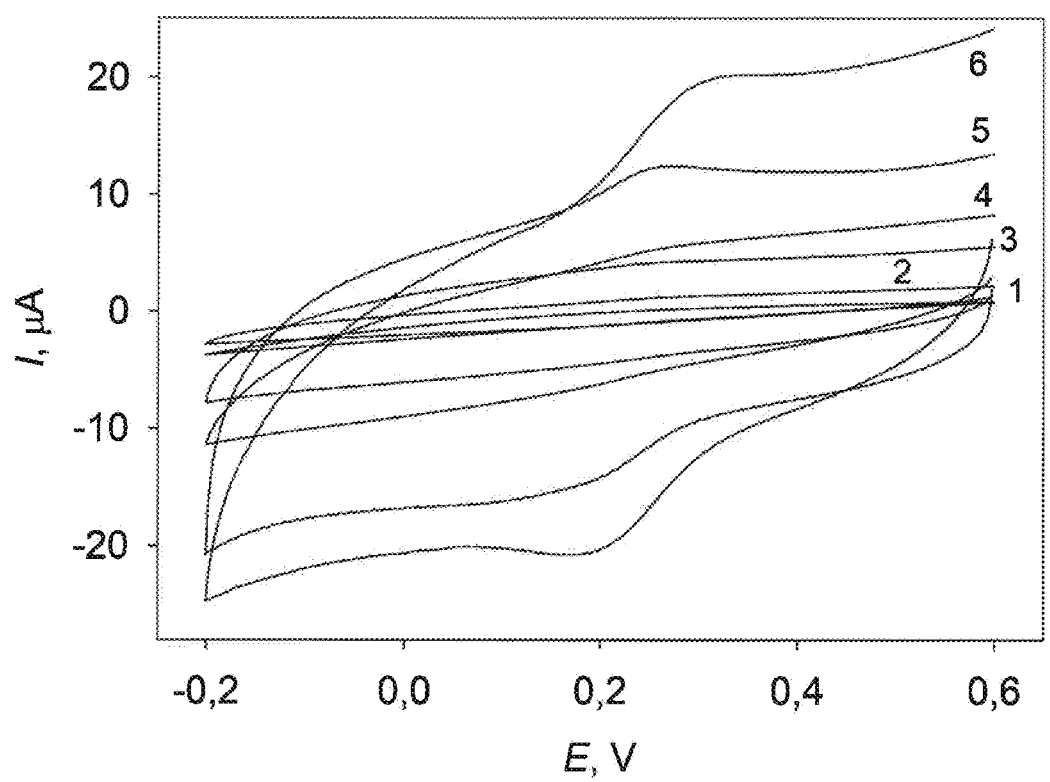
FIG. 9. Representative cyclic voltammograms recorded with nitrocellulose-modified graphite electrodes in 0.1 M PBS, pH 5, in the presence (A) and absence (B) of 1 mM K$_3$[Fe(CN)$_6$] before (1) and after treatment with magnetic beads/sandwich/cellulose assembly with E. coli cells, their concentration ranging between 1 to 10$^4$ cells/mi (2-6). Sandwich assay is performed with aptamer-aptainer combinations of capture-reporter molecules, 50 pmol OMP5 aptamer-E. coli-100 pmol OMP5 aptamer. Potential scan rate 0.1 Vs$^{-1}$.
Figure 10A:
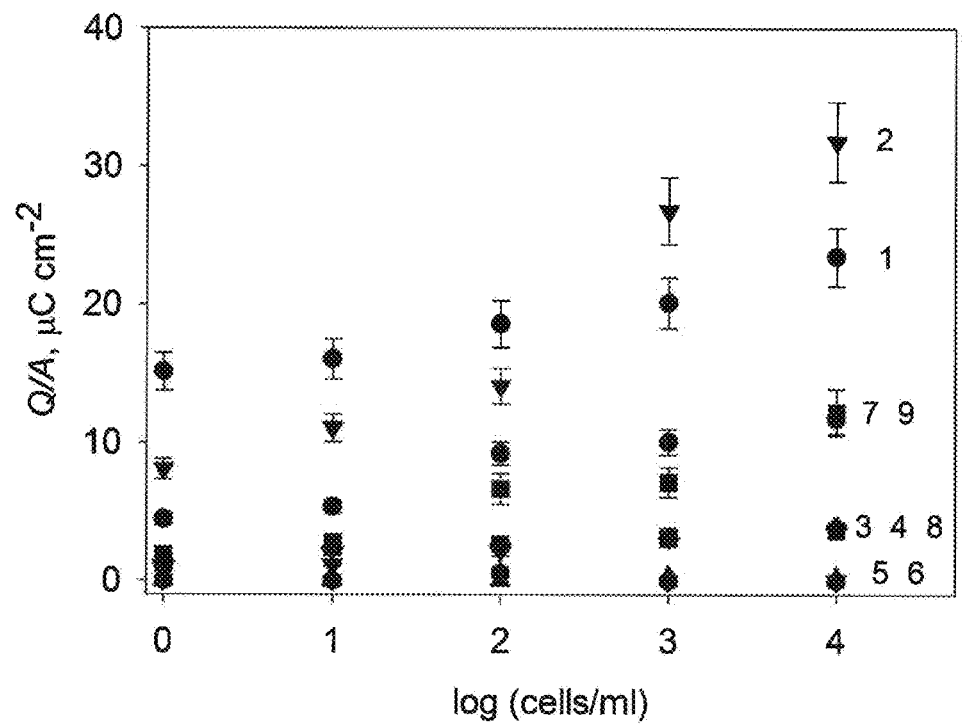
FIGS. 10A-10D show dependence of the faradaic (FIG. 10A) and capacitive (FIG. 10B) charges on the log concentration of HER2/neu protein, data derived from cyclic voltammvoltammograms recorded with nitrocellulose-modified graphite electrodes in 0.1 M PBS, pH 5, in the presence (FIG. 10A) and absence (FIG. 10B) of 1 mM K$_3$[Fe(CN)$_6$] before and after treatment with magnetic beads/sandwich/cellulase assembly with E. coli and L. brevis cells. Sandwich is assembled with different capture-reporter biomolecule combinations able of specific binding of E. coli cells.
Figure 10B:
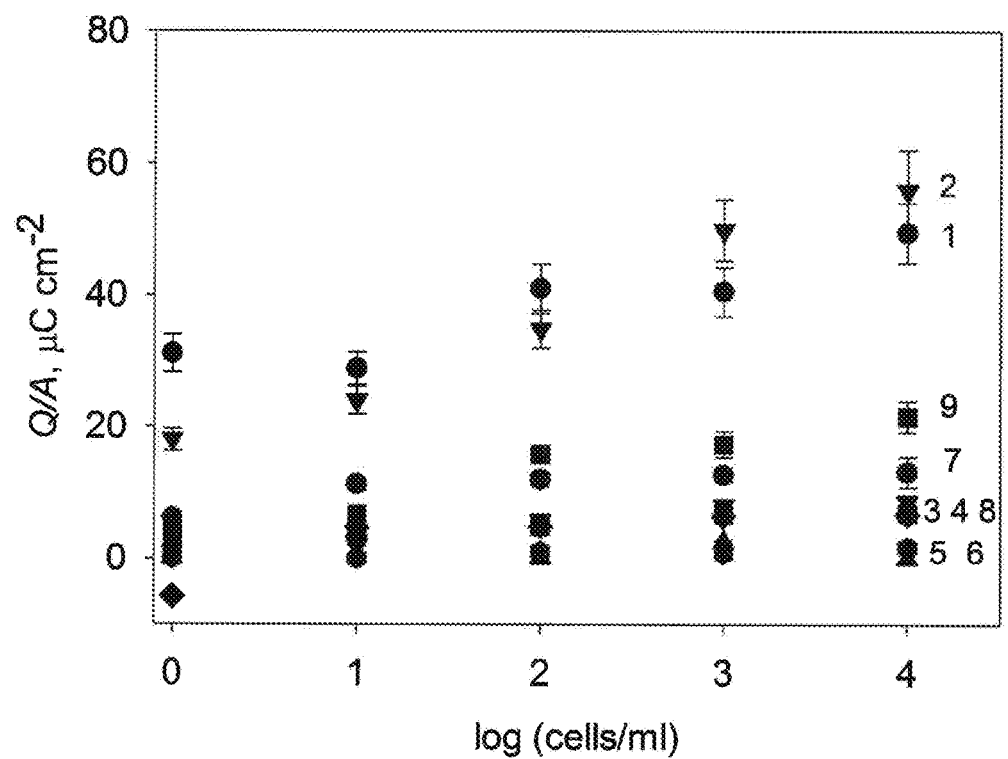

*E. coli* cells were captured and detected using different combinations of antibodies and aptamers (two different aptamer sequences Were studied) asseinbled cin MBs. All of cellulase-labelled sandwich assemblies on MBs produced the corresponding increase both in faradaic and capacitive currents recorded at the nitrocellulose-film-modified electrodes in solutions of fenicyanide (FIG. 9) and in the absence of ferricyanide. One cell in 1 ml sample could be detected. Both the Faradaic and capacitive responses and sensitivity of the analysis, reflected as a slope of the $Q_{faradaic}$ and $Q_{capacitive}$—protein concentration dependences, depended on the capture probe—reporter probe couple used, with the best performance achieved for the aptamer-cell-aptamer assemblies (FIGS. 10A-10B).

The *E-coli* OMP5 and OMP3 aptarners used have the sequence SEQ ID NO:7. OMP5 is coupled to biotin at the 5' end resulting in the following OMP5 aptamer: Biotin-5' TTT TTA TCC GTC ACA CCT CCT CTA CGG CGC TCC CAA CAG GCC TCT CCT TAC GGC ATA TTA TGG TGT TGG CTC CCG TAT-3. OMP3 is coupled to biotin at the 3' end resulting in the following OMP3 aptamer: 5'-TTT TTA TCC GTC ACA CCT GCT CTA CGG CGC TCC CAA CAG GCC TCT CCT TAC GGC ATA TTA TGG TGT TGG CTC CCG TAT-3'-Biotin.

Cell SA on MBs was performed by reacting 250 μl of MB M-280 (500 pmol ss-DNA or 50 pmol biotinylated antibody binding capability) with 1000 pmol *E. coli* OMP5/*E. coli* OMP3 or 100 pmol biotinylated E. eoli antibody for 1 hour at RT. Then, the MBs were washed three times and resuspended in 250 μl of buffer. The MB-aptamers were resuspended in the "aptamer"-buffer (containing 5 mM $Na_2HPO_4$, 2 mM $KH_2PO_4$, 150 mM NaCl, 3 mM KCl, and 1.5 mM $MgCl_2$), while the MB-antibody was resuspended in 0.1 M PBS pH 7. 10 pmol MB-aptamer or MB-antibody was reacted with 1 ml solution containing different amounts, from 1 to $10^4$ CFU/ml, of *E. coli* cells (or *Bacillus subtilis* as a control) for 1 hour at RT. Then, the MBs were washed three times and resuspended with 20 μl of buffer and allowed to react with 25 pmol of aptamer or antibody for 1 hour at RT. The mixture was washed and resuspended in 20 μl of buffer containing 25 pmol of streptavidin. The mixture was washed and resuspended with 20 μl of buffer, and 25 pmol of biotinylated cellulase was then added. Finally, the mixture was washed and resuspended in 20 μl of 0.1 M PBS, pH 5.

Figure 10C:
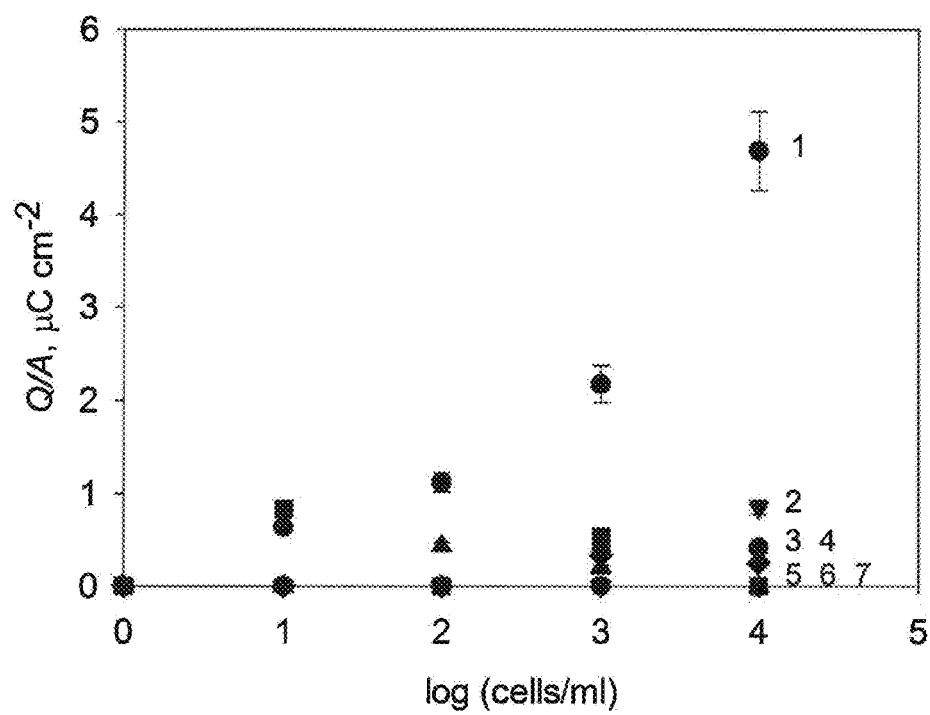
Figure 10D:
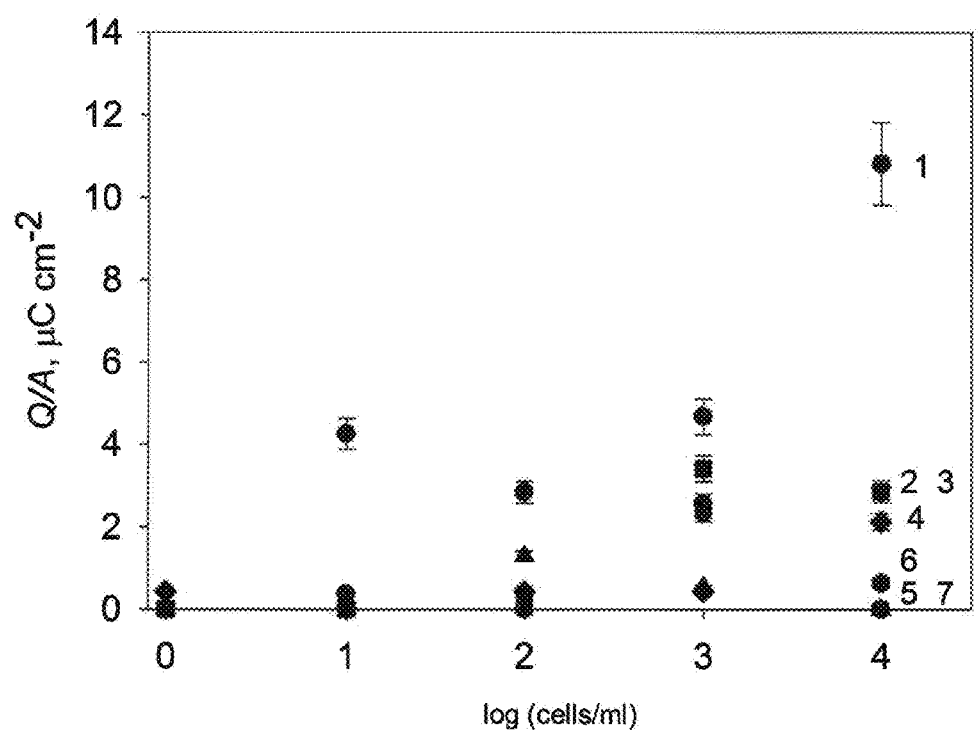
Figure 11:
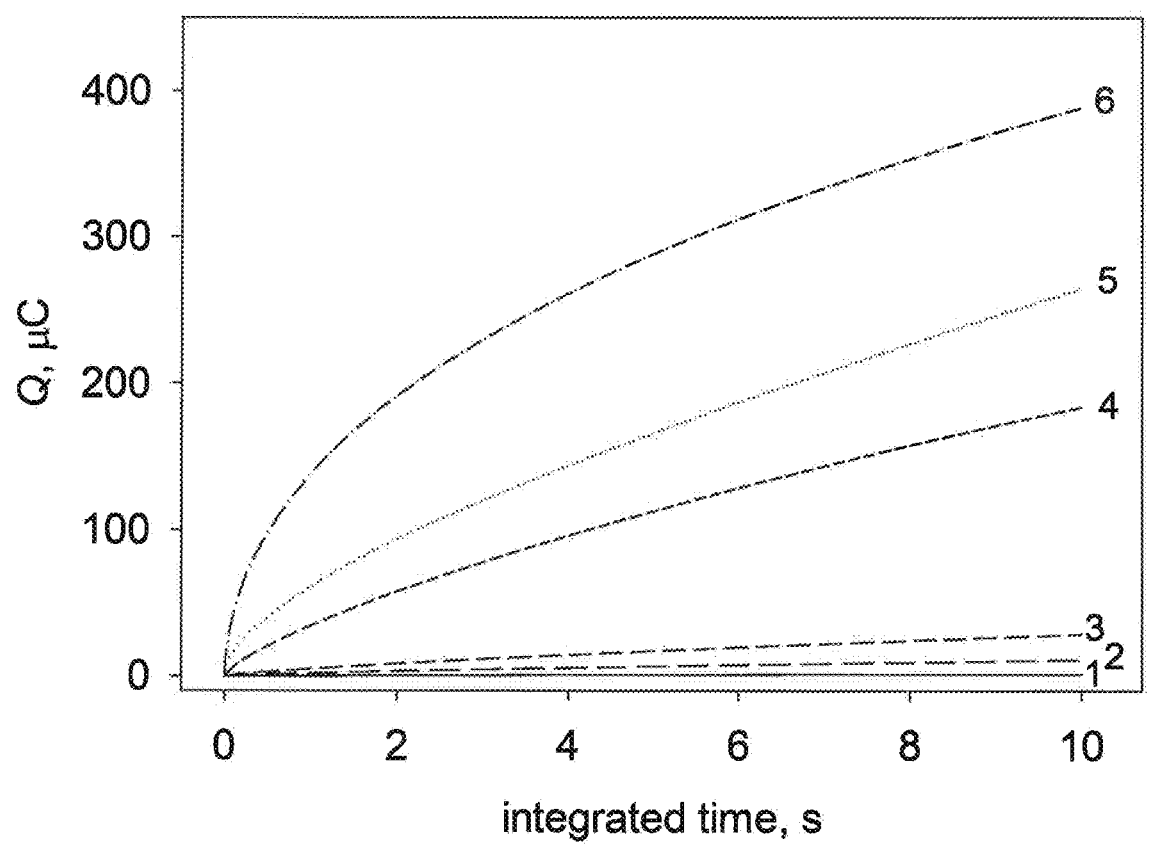
FIG. 11. Representative chronocoulometry data recorded with nitrocellulose-modified graphite electrodes in 0.1 M PBS, pH 5, before (1) and after treatment with magnetic beadsisandwichicellulase assembly with E. coli cells, their concentration ranging between 1 to 10$^4$ cells/nil (2-6). Sandwich assay is performed with Ab-OMP3 aptamer combination of capture-reporter molecules, 10 pmol capture-25 pmol reporter, Potential scan rate is 0.1 Vs$^{-1}$. Potential applied is 0 V.
Figure 12:
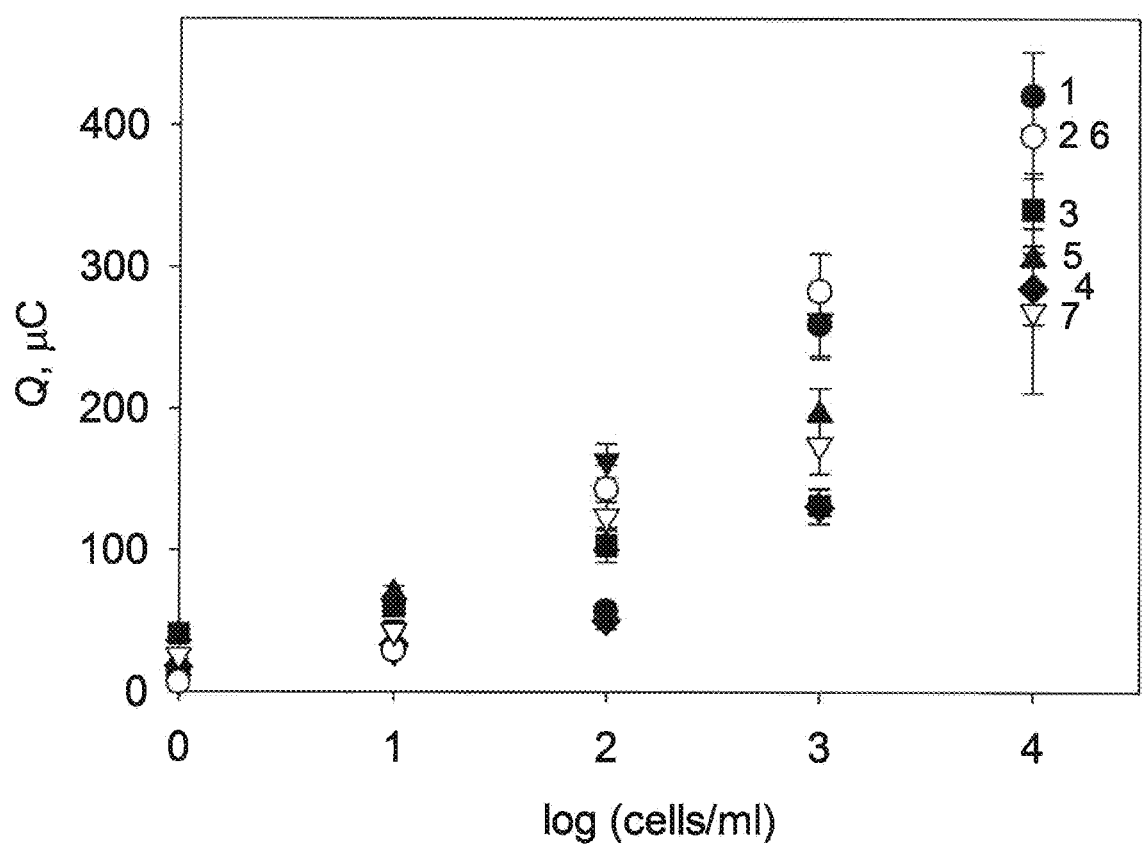
FIG. 12. Dependence of the chronocoulometric charge accumulated for 10 s on the log concentration of E. coli cells, data derived from chronocoulometry data recorded with nitrocellulose-modified graphite electrodes in 0.1 M PBS, pH 5, before and after treatment with magnetic beads/sandwich/cellulase assembly with E. coli cells. Sandwich is assembled with different aptamer and Ab capture-reporter combinations; OMP5-OMP5 (full circles, 1); OMP5-Ab (full triangles down, 2), OMP3-OMP3 (squares, 3); OMP3-Ab (diamonds, 4); Ab-OMP5 (triangles up, 5); Ab-OMP3 (empty circles, 6) and Ab-Ab (empty triangles down 7). Potential scan rate is 0.1 V s$^{-1}$. Data reflect faradaic and capacitive approaches, correspondingly.

For the OMP5 aptamer-OMP5 aptamer couple, interference from *B. subillis* cells at a concentration equal to 1000 cells/ml was less than 13-16% of the signal from 1 *E. coli* cell/ml (FIGS. 10C-10D), demonstrating specific electrochemical detection of *E. coli* cells. Even more robust and simpler analysis of *E. coli* cells was achieved by ehronocoulometric detection of the charge accumulated on the nitrocellulose electrodes that were subjected to the cellulase-lab lied sandwich on MBs capturing *E. coli* cells (FIG. 11), with the accumulated charge data plotted vs. log cell concentration exhibiting practically linear behaviour for all studied capture-reporter probes (FIG. 12).

---
Sequence list

SEQ ID NO: 1
Capture probe, L. brevis
5'-TTT TTT TTT TGG AAG CTC GTT CGA CTT A-3'

SEQ ID NO: 2
Reporter probe, L. brevis
5'-AAC TCA CCA GTT CGC CAC TTT TTT TTT-3'

SEQ ID NO: 3
Target cDNA, L. brevis
5'-TGC AAG TCG AAC GAG CTT CCG TTG AAT CGA GTG GCG AAC TGG TGA GTA ACA C-3'

---
Sequence list

SEQ ID NO: 4
Target ncDNA, L. brevis
5'-GCT TTG AGG TGC GTG TTT GTG CCT GTC CTG-3'

SEQ ID NO: 5
DNA control probe
5'-TTT TTT TTT TCT GGG AGG GAG GGA GGG CAA TTC GAA GGG GAC ACG AAA ATT G-3'

SEQ ID NO: 6
HER2-neu DNA aptamer
5'-GCA GCG GTG TGG GGG CAG CGG TGT GGG GGC AGC GGT GTG GGG TTT TT-3'

SEQ ID NO: 7
E-coli OMP DNA aptamer
5'-TTT TTA TCC GTC ACA CCT GCT CTA CGG CGC TCC CAA CAG GCC TCT CCT TAC GGC ATA TTA TGG TGT TGG CTC CCG TAT-3'

---

Items

1. A method for determining, the presence and/or the concentration of an analyte in a sample, said method comprising:
    contacting said sample with a solution comprising
    magnetic beads
    a capture probe capable of binding said analyte
    a reporter probe
    cellulase
    whereby, if the analyte is present, an MB-analyte-reporter-cellulase sandwich is formed;
       contacting said solution comprising said sandwich with an electrode covered with an electrically insulating layer comprising or consisting of cellulose and/or a cellulose derivative
    wherein the MB-analyte-reporter-cellulase sandwich leads to degradation of the insulating layer thereby causing a measurable change in electrical properties at the electrode surface, wherein said change in electrical properties is a function of the amount of analyte in said sample.
2. The method according to item 1, wherein cellulase is added to the solution after addition of the magnetic beads, the capture probe and the reporter probe, such that, if the analyte is present, an MB-analyte-reporter complex is formed before addition of cellulose.
3. The method according to any of items 1 and 2, wherein said reporter probe is added to the solution after addition of the magnetic beads and the capture probe, such that, if the analyte is present, an MB-analyte complex is formed before addition of reporter probe.
4. The method according to item any of the preceding items further comprising a step of isolating said MB-analyte complexes, MB-analyte-reporter complexes or MB-analyte-reporter-cellulase sandwiches from the sample using a magnet.
5. The method according to any of the preceding items, wherein said analyte is an oligonucleotide.
6. The method according to any of items 1 to 4, wherein said analyte is a protein.
7. The method according to any of items 1 to 4, wherein said analyte is a cell.
8. The method according to any of the preceding items, wherein said magnetic beads are chemically modified with streptavidin, avidin, gold, biotin, or polymers such as dextrane and chitosan.

9. The method according to any of the preceding items, wherein said capture probe is a oligonucleotide, an antibody or an aptamer.
10. The method according to item 9, wherein said oligonucleotide is biotinylated.
11. The method according to any of items 9 and 10, wherein said oligonucleotide is biotinylated DNA.
12. The method according to any of the preceding items, wherein said reporter probe is an oligonucleotide, an antibody or an aptamer.
13. The method according to item 12, wherein said oligonucleotide is biotinylated.
14. The method according to any of items 12 and 13, wherein said oligonucleotide is biotinylated DNA.
15. The method according to any of the preceding items, wherein said cellulase is biotinylated or conjugated with streptavidin or avidin.
16. The method according to any of the preceding items, wherein said insulating layer comprises or consists of nitrocellulose.
17. A device for measuring the concentration of an analyte, wherein said device comprises an electrode covered with an electrically insulating layer comprising or consisting of cellulose or cellulose derivatives, wherein said electrode is embedded in a solution comprising magnetic beads, a capture probe and a reporter probe, wherein addition of analyte and cellulose to said solution leads to the formation of a sandwich leading to a cellulase mediated degradation of the nitrocellulose layer thereby causing a measurable change in electrical properties at the electrode surface, wherein said change in electrical properties is a function of the amount of analyte in said sample.
18. The device according to item 17, wherein said solution further comprises cellulase.
19. The device according to any of item 17 to 18, wherein said analytes as defined in any of items 5 to 7.
20. The device according to any of items 17 to 19, wherein said capture probe is as defined in any of items 9 to 11.
21. The device according to any of items 17 to 20, wherein said reporter probe is as defined in any of items 12 to 14.
22. The device according to any of items to 21, wherein said insulating layer comprises or consists of nitrocellulose.
23. A biosensor comprising the device according to any of items 17 to 22,
24. A kit comprising an electrode covered with an electrically insulating layer comprising or consisting of cellulose or cellulose derivatives, magnetic, beads, a capture probe, a reporter probe and cellulose.
25. The kit according to item 24, wherein said analyte is as defined in any of items 5 to 7.
26. The kit according to any of items 24 to 25, wherein said capture probe is as defined in any of items 9 to 11.
27. The kit according to any of items 24 to 26, wherein said reporter probe is as defined in any of items 12 to 14.
28. The kit according to any of items 24 to 27, wherein said insulating layer comprises or consists of nitrocellulose.

The invention claimed is:

1. A device for measuring the concentration of an analyte, wherein said device comprises an electrode covered with an electrically insulating layer comprising or consisting of cellulose or cellulose derivatives, wherein said covered electrode is embedded in a solution comprising magnetic beads, a capture probe bound to a magnetic bead, and a reporter probe bound to cellulase.

2. The device according to claim 1, wherein said analyte is an oligonucleotide, a protein or a cell.

3. The device according to claim 1, wherein said capture probe is an oligonucleotide, a biotinylated oligonucleotide, biotinylated DNA, an antibody or an aptamer.

4. The device according to claim 1, wherein said reporter probe is an oligonucleotide, a biotinylated oligonucleotide, biotinylated DNA, an antibody or an aptamer.

5. The device according to claim 1, wherein said insulating layer comprises or consists of nitrocellulose.

6. The device according to claim 1, wherein said device is a biosensor.

7. A kit for measuring the concentration of an analyte comprising an electrode covered with an electrically insulating layer comprising or consisting of cellulose or cellulose derivatives, magnetic beads, a capture probe bound to a magnetic bead, a reporter probe bound to cellulase, wherein:
   said analyte is an oligonucleotide, a protein or a cell;
   said capture probe is an oligonucleotide, a biotinylated oligonucleotide, biotinylated DNA, an antibody or an aptamer;
   said reporter probe is an oligonucleotide, a biotinylated oligonucleotide, biotinylated DNA, an antibody or an aptamer; and
   said insulating layer comprises or consists of nitrocellulose.

* * * * *